(12) United States Patent
van Hemert et al.

(10) Patent No.: US 9,329,046 B2
(45) Date of Patent: May 3, 2016

(54) METHODS AND SYSTEMS GENERATING DRIVER WORKLOAD DATA

(71) Applicant: TomTom International B.V., Amsterdam (NL)

(72) Inventors: Jasper-Michiel van Hemert, Utrecht (NL); Michel Alders, Amsterdam (NL)

(73) Assignee: TomTom Navigation B.V., Amsterdam (NL)

( * ) Notice: Subject to any disclaimer, the term of this patent is extended or adjusted under 35 U.S.C. 154(b) by 0 days.

(21) Appl. No.: 14/411,645

(22) PCT Filed: Jul. 1, 2013

(86) PCT No.: PCT/EP2013/063856
§ 371 (c)(1),
(2) Date: Dec. 29, 2014

(87) PCT Pub. No.: WO2014/001575
PCT Pub. Date: Jan. 3, 2014

(65) Prior Publication Data
US 2015/0160020 A1   Jun. 11, 2015

(30) Foreign Application Priority Data
Jun. 29, 2012   (GB) .................................. 1211633.1

(51) Int. Cl.
*B60W 40/00*   (2006.01)
*G01C 21/00*   (2006.01)
(Continued)

(52) U.S. Cl.
CPC . *G01C 21/26* (2013.01); *A61B 5/18* (2013.01); *G01C 21/3484* (2013.01); *G01C 21/3641* (2013.01); *A61B 5/0533* (2013.01); *A61B 5/1112* (2013.01); *B60W 40/09* (2013.01)

(58) Field of Classification Search
USPC ......................................................... 701/400
See application file for complete search history.

(56) References Cited

U.S. PATENT DOCUMENTS 7,216,022 B2   5/2007   Kynast et al.
7,353,111 B2   4/2008   Takahashi et al.
(Continued)

FOREIGN PATENT DOCUMENTS

EP   1596162 A1   11/2005
JP   H10253379 A   9/1998
(Continued)

OTHER PUBLICATIONS

Search Report issued Sep. 27, 2012 for United Kingdom Patent Application No. GB1211633.1.
(Continued)

*Primary Examiner* — Yonel Beaulieu

(57) ABSTRACT

A method of determining data indicative of an individual driver workload is disclosed. The method involves obtaining a generic driver workload parameter, the generic driver workload data being based on data indicative of the behavior of multiple drivers when performing a maneuver at a node or traversing a set of one or more segments of an electronic map. An individual modifier representative of the behavior of an individual driver is generated and used to determine an individual driver workload parameter indicative of the workload of the individual driver when performing the maneuver at a node or traversing the one or more segments of an electronic map based on the generic driver workload data for performing the maneuver at the node or traversing the one or more segments of the electronic map.

19 Claims, 3 Drawing Sheets

(51) Int. Cl.
*G01C 21/26* (2006.01)
*A61B 5/18* (2006.01)
*G01C 21/34* (2006.01)
*G01C 21/36* (2006.01)
*B60W 40/09* (2012.01)
*A61B 5/053* (2006.01)
*A61B 5/11* (2006.01)

(56) References Cited

U.S. PATENT DOCUMENTS

| | | | |
|---|---|---|---|
| 7,394,393 B2 | 7/2008 | Zhang et al. | |
| 7,532,958 B2 | 5/2009 | Powers et al. | |
| 2005/0234617 A1 | 10/2005 | Kynast et al. | |
| 2005/0256635 A1* | 11/2005 | Gardner | G01C 21/26 701/431 |
| 2006/0015219 A1 | 1/2006 | Kynast et al. | |
| 2006/0293799 A1 | 12/2006 | Powers et al. | |
| 2007/0063854 A1 | 3/2007 | Zhang et al. | |
| 2007/0124027 A1* | 5/2007 | Betzitza | B60W 40/02 701/1 |
| 2007/0219672 A1* | 9/2007 | Fehr | B60W 40/08 70/1 |
| 2009/0157294 A1 | 6/2009 | Geelen et al. | |
| 2009/0298482 A1* | 12/2009 | Yen | H04M 1/6075 455/414.2 |
| 2010/0274440 A1 | 10/2010 | Kim et al. | |

FOREIGN PATENT DOCUMENTS

| | | |
|---|---|---|
| JP | 2007322249 A | 12/2007 |
| WO | 2008004857 A1 | 1/2008 |
| WO | 2009143903 A1 | 12/2009 |

OTHER PUBLICATIONS

International Search Report issued Sep. 19, 2013 for International Patent Application No. PCT/EP2013/063856.

* cited by examiner

METHODS AND SYSTEMS GENERATING DRIVER WORKLOAD DATA

CROSS-REFERENCES TO RELATED APPLICATIONS

This application is the National Stage of International Application No. PCT/EP2013/063856, filed Jul. 1, 2013 and designating the United States. The application claims priority from United Kingdom Patent Application No. 1211633.1 filed Jun. 29, 2012. The entire content of both these applications is incorporated herein by reference.

FIELD OF THE INVENTION

The present invention relates to methods and systems for determining data indicative of the workload of a driver. In particular, the present invention is concerned with determining data indicative of the workload of an individual driver in respect of a given manoeuvre at a node or the traversal of a set of one or more segments of an electronic map.

BACKGROUND TO THE INVENTION

In recent times driver workload, and its impact upon driver performance, has attracted increasing interest. Driver workload is representative of the demands placed on a driver while driving, and is based on a primary contribution in respect of the main task of driving, and a secondary contribution in respect of peripheral activities, for example use of in-vehicle systems, e.g. navigation devices such as personal navigation devices (PNDs) or integrated navigation devices, or Advanced Driver Assistance Systems (ADAS). Driver workload as used herein may also be referred to as "driver mental workload", and references to "driver workload" may be replaced with references to "driver mental workload".

A driver's mental capacity must be sufficient to attend to the primary task of driving and any peripheral activities. Any increase in driver workload required by in-vehicle systems will take up mental capacity, and will reduce the mental capacity available to attend to the task of driving, potentially compromising safety. The task of driving may require differing amounts of mental capacity under different circumstances, e.g. weather, lighting, etc, and depending upon the individual driver, e.g. age, experience, particular difficulties, etc. It is important therefore to balance the level of driver workload associated with in-vehicle systems for different circumstances and for different drivers, taking into account the mental capacity required to perform the main function of driving.

Understanding driver workload is therefore important in designing in-vehicle systems, to ensure that the systems support the driver, and avoid overburdening the driver. Systems, and in particular their communication with a driver, may be adapted depending upon a predicted or detected workload for a given set of circumstances. For example, certain functions may be disabled to allow the driver to focus on the task of driving, or a display or other output of a system may be altered to control the amount of information presented to the driver at any time depending upon the determined workload.

Various techniques have been proposed for measuring or otherwise determining driver workload. This may involve sensing of certain parameters indicative of workload, including parameters indicative of driving style, behavioural and psychological parameters. Driver workload levels may be assessed by reference to detected parameters relating to the individual driver, and may take into account historic behaviour of the driver. A driver profile may be generated for a given driver indicative of workload when performing different activities. For example, various known methods of assessing driver workload, and adjusting the operation of in-vehicle systems in dependence on the assessed workload level, are described in US 2006/0293799 A1, US 2007/0124027 A1, US 2005/0234617 A1 and US 2006/0015219 A1.

The Applicant's co-pending application, published as WO 2008/004857 A1, and entitled "Navigation Device with Adaptive Navigation Instructions", discloses a navigation device in which navigation instructions are adapted according to an individual driver profile, in order to better conform to the drivers preferences and to contribute to safer behaviour. The driver profile may be based on parameters reflecting driver preferences or habits. The driver profile parameters may include parameters derived from driver input information or preferences, and also parameters based on detected behaviour of a driver. For example, the ability of a driver to follow route navigation instructions under different conditions e.g. different times of day, week or year, weather or lighting conditions etc may be detected, and used in providing the profile. The navigation instructions output by the device are adapted based upon the profile data using a "profile-to-instruction translator". For example, the density or detail of instructions may be adjusted, mode of output, e.g. whether visual or audible, etc. The entire contents of WO 2008/004857 A1 is incorporated herein by reference.

Another co-pending application of the Applicant, published as WO 2009/143903 A1, and entitled "Navigation Apparatus and Method that Adapt to Driver's Workload", discloses a navigation apparatus in which the workload of the driver is determined and used to provide or alter communication with the driver dependent upon the determined workload of a driver at a given time. The workload parameter may be based on various factors including sensed physiological parameters, psychological parameters, environmental factors, external factors and dynamic factors, and may be based in part upon driver input data. The drivers behaviour may be assessed by reference to that of other drivers. For example, where the drivers speed is found to be less than or greater than an average speed of other traffic surrounding the driver at that time, or less than or greater than a historical average speed for the relevant section of road, this may be indicative of fatigue or stress respectively. An individual historical driver profile may be determined which can be used in the calculation of driver workload. The driver profile may be updated and changes in the profile used as a measure of driver workload. The workload information may be used in various ways to control communication with the driver e.g. adjusting frequency or mode of instructions, adjusting display of instructions. The application also discloses that historical driver profile data may be used to provide a data map, indicative of a variation in driver workload throughout a road network. The entire contents of WO 2009/143903 A1 is also incorporated herein by reference.

Although considerable effort has been directed to the determining of driver workload, and its use in controlling the operation of in-vehicle systems (and devices that can be removably mounted within vehicles), the Applicant has realised that there remains a need for improved methods and systems for determining the workload of an individual driver.

SUMMARY OF THE INVENTION

In accordance with a first aspect of the present invention there is provided a method of determining data indicative of an individual driver workload, the method comprising:

obtaining generic driver workload data, the generic driver workload data being representative of a generic driver workload when performing a manoeuvre at a node or traversing a set of one or more segments of an electronic map;

generating an individual modifier representative of the behaviour of an individual driver; and using the individual modifier to determine individual driver workload data indicative of the workload of the individual driver when performing the manoeuvre at the node or traversing the one or more segments of the electronic map based on the generic driver workload data for the manoeuvre at the node or the traversal of the one or more segments.

In accordance with the invention therefore, generic driver workload data, e.g. a generic driver workload parameter, is obtained indicative of driver workload when performing a given manoeuvre at a node or traversing one or more segments of an electronic map. In addition, an individual modifier value is generated based on the behaviour of an individual driver which is used to determine driver workload data, e.g. an individual workload parameter, for the individual driver indicative of the workload of the individual driver when performing the manoeuvre at the node or traversing the one or more segments based on the generic driver workload data. In other words, the modifier enables individual driver workload data to be determined for the manoeuvre or traversal of segment(s) based upon the generic workload data.

The generic driver workload data forms a base for determining the individual driver workload data using the modifier which has a basis in the real-life behaviour of the individual driver. Determining individual driver workload data in this way, by modifying a generic template using data reflecting the behaviour of an individual driver, has been found to be particularly advantageous. Modifying a base template may provide a more efficient way of obtaining individual driver workload data, by suitably customising the generic template, without needing to collect large amounts of data regarding the individual driver and their behaviour. For example, once a suitable base template is established, which may be a pre-existing template, individual driver workload data may be obtained based on the template for any manoeuvre at a node, or traversal of a segment or segments using a limited set of personal modifiers, or even a single personal modifier value. The generic driver workload data may form part of a generic driver workload profile, including generic driver workload data, e.g. parameters in respect of different manoeuvres at nodes and/or the traversal of different segments of an electronic map. Thus, the generic driver workload data may provide a base template for workload, incorporating variation with respect to different manoeuvres or positions on an electronic map. Obtaining the individual driver workload relative to the generic driver workload data of such a profile using an individual driver modifier may then, even if the individual driver modifier used is the same for each manoeuvre or position, result in a varying individual driver workload for different manoeuvres or positions in accordance with the generic driver workload profile.

The present invention resides in the combination of the use of generic driver workload data, and an individual driver workload modifier based on individual driver behaviour, to obtain individual workload data for the individual driver.

The present invention extends to a system for carrying out any of the steps of the methods herein described. Thus, in accordance with a further aspect of the invention there is provided a system, optionally an in-vehicle device or a server, for determining data indicative of an individual driver workload, the system being configured to:

obtain generic driver workload data, the generic driver workload data being representative of a generic driver workload when performing a manoeuvre at a node or traversing a set of one or more segments of an electronic map;

generate an individual modifier representative of the behaviour of an individual driver; and use the individual modifier to determine individual driver workload data indicative of the workload of the individual driver when performing the manoeuvre at the node or traversing the one or more segments of the electronic map based on the generic driver workload data for the manoeuvre at the node or the traversal of the one or more segments.

Where not explicitly stated, it will be appreciated that the invention in any of its aspects may include any or all of the features described in respect of other aspects or embodiments of the invention to the extent they are not mutually exclusive. In particular, while various embodiments of operations have been described which may be performed in the method and by the system or apparatus, it will be appreciated that any one or more or all of these operations may be performed in the method and by the system or apparatus, in any combination, as desired, and as appropriate.

In accordance with the invention in the further aspect, the system may comprise means for carrying out any of the steps described, which may be a set of one or more processors. Any reference to "means for", or the system being arranged to carry out a given step, may be replaced by a reference to a set of one or more processors for carrying out the step or steps.

It will be appreciated that the methods of the present invention may be implemented by means of a distributed system. The steps of the methods described herein may be performed exclusively on a server, or some on a server and the others on a navigation device in any combination, or exclusively on a navigation device. Performance of one or more of the steps on the server may be efficient and may reduce the computational burden placed on a navigation device. Alternatively if one or more steps are performed on the navigation device, this may reduce any bandwidth required for network communication.

In accordance with a further aspect of the invention there is provided a method comprising:

obtaining generic driver workload data, the generic driver workload data being representative of a generic driver workload when performing a manoeuvre at a node or traversing a set of one or more segments of an electronic map; and generating an individual modifier representative of the behaviour of an individual driver for use in determining individual driver workload data indicative of the workload of the individual driver when performing the manoeuvre at the node or traversing the one or more segments of an electronic map based on the generic driver workload data for performing the manoeuvre at the node or traversing the one or more segments of the electronic map.

In accordance with a further aspect of the invention there is provided a system, optionally a server, arranged to:

obtain generic driver workload data, the generic driver workload data being representative of a generic driver workload when performing a manoeuvre at a node or traversing a set of one or more segments of an electronic map; and generate an individual modifier representative of the behaviour of an individual driver for use in determining individual driver workload data indicative of the workload of the individual driver when performing the manoeuvre at the node or traversing the one or more segments of an electronic map based on the generic driver workload data for performing the manoeuvre at the node or traversing the one or more segments of the electronic map.

The present invention in accordance with these further aspects may include any or all of the features described in relation to the other aspects or embodiments of the invention. It will be appreciated that, in respect of these further aspects of the invention that do not refer to the step of using the individual modifier to obtain the individual driver workload data, this step may be omitted from any of the embodiments of the method described below.

In accordance with the invention in any of its aspects described herein, for the avoidance of doubt, references to "generic driver workload data", "generic driver workload profile" or "generic driver workload parameter" should be understood to refer to, and may be replaced by, a reference to data indicative of generic driver workload, generic driver workload profile, or generic driver workload parameter respectively, and may be any data indicative thereof. Likewise "individual driver workload data", "individual driver workload profile" or "individual driver workload parameter" should be understood as referring to, and may be substituted by, references to data indicative of an individual driver workload, an individual driver workload parameter, or individual driver workload profile respectively. Similarly the term "individual modifier" may be referred to as "individual modifier data" or data indicative of an individual modifier. Any reference to the terms occurring herein should therefore be understood as encompassing data indicative of the specified parameter, profile or modifier, and may be replaced by such a term.

In accordance with the invention, the data indicative of generic driver workload for performing the given manoeuvre at a node or traversing a set of one or more segments of an electronic map, may be of any suitable form, and may include one or more values indicative of workload. The data may be in absolute or relative terms. Preferably the generic driver workload data is a generic driver workload parameter for performing the manoeuvre or traversing the set of one or more segments. References to generic driver workload data herein may be replaced by a reference to a generic driver workload parameter.

The generic driver workload data is representative of a generic driver workload when performing a given manoeuvre at a node and/or traversing one or more segments of an electronic map in relation to which individual driver workload data is to be determined. The generic driver workload data may be of any form, provided that is indicative of a generic, rather than individual workload. Preferably the generic driver workload data is indicative of an average driver workload when performing the manoeuvre at the node and/or traversing the one or more segments of the map.

The data may be obtained using suitable theoretical modelling techniques. It is envisaged that generic workload data might be obtained based on the properties of the manoeuvre and/or the node at which the manoeuvre is to be performed, or, in the case of the traversal of a set of one or more segments, based upon one or more attributes of the segments, or the set of segments. The data may be based upon a complexity of a manoeuvre or the traversal of one or more segments (e.g. based upon the complexity of any manoeuvres or junctions need to be traversed). In embodiments the data may additionally or alternatively be based upon a geometry of the node or segment(s). For example, the generic workload data might be determined based upon, e.g. a curvature of the segment(s) involved, whether a manoeuvre is a right or left turn, etc. In some embodiments, therefore, the generic workload data may be determined, optionally entirely, based upon electronic map data.

However, in particularly preferred embodiments, the generic workload data is representative of the behaviour of multiple drivers when performing the manoeuvre and/or traversing the one or more segments. Thus, the generic workload data and/or is preferably based upon data indicative of the behaviour of multiple drivers when performing the manoeuvre and/or traversing the one or more segments. The data may be based at least in part, and preferably entirely on the behaviour of multiple drivers. This has the advantage that the resulting generic workload data will be based upon the real life behaviour of multiple drivers. Using such data is advantageous in providing more accurate individual workload data, taking into account workload variation due to human factors which may be difficult to predict using theoretical models. Preferably the data is then based upon the historical behaviour of multiple drivers when performing the manoeuvre or traversing the one or more segments. It will be appreciated that the generic driver workload data is specific to a given manoeuvre, or the traversal of a set of one or more segments of an electronic map.

Data indicative of a generic driver workload based upon the behaviour of multiple drivers may be determined in any of the manners known in the art for determining data indicative of the behaviour of an individual driver. The data may be based upon data indicative of any behaviour which is somehow indicative of driver workload, and may be based upon any of the detected behaviour(s), and obtained in any of the manners described in more detail below in relation to determining behaviour of an individual driver for determining the individual modifier. The data may be based upon a distribution representative of the behaviour of multiple drivers when performing the manoeuvre at the node or nodes and/or traversing the one or more segments of the map. For example, the data may be indicative of a percentile behaviour. Preferably the generic driver workload data is indicative of an average driving behaviour when performing the manoeuvre at the node and/or traversing the one or more segments of the map.

In preferred embodiments the generic driver workload data forms part of a generic driver workload profile comprising data indicative of a generic workload of drivers, e.g. a generic driver workload parameter, when performing each of plurality of different manoeuvres at a node or nodes and/or traversing a plurality of sets of one or more segments of the electronic map. The profile may then comprise generic driver workload data e.g. a parameter in respect of some or all of the manoeuvres or possible traversals of segments in the area covered by the electronic map. For example, data may only be provided in respect of certain more challenging manoeuvres or segment(s). The method may comprise obtaining, e.g. accessing or generating, such a profile.

The generic driver workload data indicative of the generic driver workload when performing the manoeuvre at a node or traversing the one or more segments of the electronic map is preferably associated with electronic map data indicative of the manoeuvre at a node, or the one or more segments of the electronic map to which it relates. Where the parameter relates to a manoeuvre at a node, the parameter is preferably associated with data indicative of the manoeuvre, i.e. type of turn, etc, and the node. In some embodiments generic driver workload data, e.g. a generic driver workload parameter, may be provided as an attribute of the node and/or one or more segments to which it relates.

In preferred embodiments therefore, the generic driver workload data is associated with electronic map data. The electronic map data is indicative of the manoeuvre at a node or the one or more segments to which it relates. In some preferred embodiments in which the generic driver workload data forms part of a generic driver workload profile, the profile comprises generic driver workload data for a plurality of manoeuvres at a node and/or the traversal of a plurality of sets of segments of the electronic map, the generic driver workload data being associated with electronic map data indicative of the manoeuvre and/or the set of one or more segments to which it relates. For example, the generic driver workload profile may be provided as a map layer. In other words, the data is provided as an additional data layer to enhance a base electronic map layer containing the underlying electronic map data. This is in a similar manner to that in which other additional data layers representing attributes of map segments or nodes may be provided, e.g. relating to (time dependent) average speeds, etc. The map data may or may not be stored separately to the workload parameter(s).

The step of obtaining the generic driver workload data in accordance with the invention may be carried out before or after, or even at the same time as, the step of generating the individual modifier. In preferred embodiments, the step of generating the individual modifier is not carried out by reference to the generic driver workload data for the given manoeuvre or segments to be traversed, e.g. where the same individual modifier is to be applicable to determining individual workload data in respect of different manoeuvres or the traversal of different sets of segments. In some embodiments, electronic map data identifying the relevant manoeuvre or segments in relation to which individual workload data is to be determined may be referred to, e.g. in order to identify a suitable modifier. It will be appreciated that generic driver workload data may be based upon multiple factors. For example the data may be based in part upon the behaviour of multiple drivers when performing a manoeuvre or traversing a set of one or more segments, and may be based in part upon other factors, e.g. a theoretical workload, workload detected other than by reference to the behaviour of the driver, e.g. based upon physiological or psychological responses, etc.

The generic driver workload data may be obtained in any manner. In some embodiments the step of obtaining the data may comprise accessing the data, e.g. from a database. Thus, the data may be pre-existing generic driver workload data which need not have been generated for the purposes of the present invention. The step of obtaining the generic driver workload data may be carried out by a server.

The present invention may extend to generating the generic driver workload data in accordance with any of the embodiments described. In some embodiments the step of obtaining the generic driver workload data comprises generating the data and, in embodiments, associating the data with electronic map data indicative of the manoeuvre at a node or one or more segments of the electronic map to which it relates. Preferably the generic driver workload data is based upon the behaviour of multiple drivers when performing the manoeuvre at a node or traversing the set of one or more segments. The method may comprise collecting data indicative of the behaviour of multiple drivers when performing the manoeuvre or traversing the one or more segments, and using the data to obtain the generic driver workload data. The method may comprise determining a generic workload that is an average workload based upon the behaviour of the multiple drivers. The method may involve any suitable processing and/or filtering of the results.

In preferred embodiments generic driver workload data is obtained in respect of a plurality of manoeuvres at a node and/or the traversal of a plurality of sets of one or more segments of an electronic map. This may be referred to as a generic driver workload profile. Accordingly, in embodiments the method may extend to generating a generic driver workload profile in accordance with any of the embodiments described above.

Generic driver workload data or a generic driver workload profile may be obtained in any suitable manner. As discussed above, methods of obtaining generic driver workload data, e.g. parameters in respect of a manoeuvre at a node or traversal of one or more segments, or generic driver workload profiles containing such information associated with electronic map data are known in the art. Suitable methods are described, for example, in WO 2009/143903 A1.

In accordance with the present invention in any of its aspects or embodiments, the generated individual modifier can be, and in accordance with the invention in certain aspects, is, used to determine individual driver workload data indicative of the workload of the individual driver when performing the manoeuvre at a node or traversing the one or more segments of the electronic map based on the generic driver workload data.

As discussed above, in some preferred embodiments, the step of generating the individual modifier is carried out by a server. The step of using the individual modifier to determine the individual driver workload may be carried out by a server, or, in embodiments, the method may comprise a server transmitting the generated individual modifier to a remote system, e.g. an in-vehicle system such as a navigation device or ADAS, with the in-vehicle system carrying out the step of determining the individual driver workload. In other embodiments, the modifier may be stored by the server, and a remote system, e.g. in-vehicle system, may then access the modifier data when individual driver workload data is to be determined.

In accordance with the invention in any of its aspects or embodiments, the individual modifier is representative of the behaviour of the individual driver. The individual modifier is preferably generated using data representative of the behaviour of an individual driver. The present invention extends to the step of obtaining such data and using the data in generating the individual modifier. In embodiments the method comprises obtaining data indicative of the behaviour of an individual driver and generating the individual modifier using the data. The step of obtaining the data may comprise receiving the data, preferably from an in-vehicle system.

In some preferred embodiments the step of generating the individual modifier is carried out by a server. For example, the individual modifier may be generated by the server using data indicative of the behaviour of the individual driver which may be generated remotely. In preferred embodiments the data indicative of the behaviour of the individual driver is obtained by an in-vehicle system and provided to the server. In these embodiments the server receives the data from an in-vehicle system. For example, the server may receive such data directly or indirectly from an in-vehicle system. The in-vehicle system may be a navigation device, e.g. a personal navigation device (PND) or integrated device, or an ADAS system. In some embodiments the method comprises the in-vehicle system transmitting the data to the server. In other embodiments the data may first be uploaded, e.g. from a navigation device to a computer apparatus, e.g. a laptop, desktop or other computer apparatus, e.g. of the driver, and then uploaded to the server. Of course, the data may be obtained by an in-vehicle system in embodiments in which the individual modifier is not determined by a server. For example, the data may be provided to another processing device, or may be used by the in-vehicle system to obtain the modifier.

The individual modifier may be generated using data representative of the real-time or historic behaviour of the individual driver, or combinations thereof. The data indicative of driver behaviour is based at least in part, and, in some embodiments, entirely, upon data indicative of the actual driving behaviour of the driver, whether real-time, historic, or combinations thereof. Of course, the individual modifier may be based at least in part upon data obtained from other sources, e.g. being provided by the driver, such as in response to questions, data indicative of the workload of the driver sensed in other manners, e.g. using psychological or physiological sensing, and which may or may not be provided specifically for the purpose of the present invention.

The individual modifier is representative of the behaviour of the individual driver, and therefore provides an indication of how the generic workload data, e.g. parameter should be varied to provide individual workload data, e.g. a parameter for the driver concerned. The individual modifier may be representative of the behaviour of the individual driver relative to a generic behaviour of drivers, e.g. relative to an average behaviour. Knowledge of the behaviour of the individual driver provides a way of estimating the likely deviation of individual workload of the driver when performing a manoeuvre or traversing one or more segments by comparison to an average or generic workload of drivers.

The individual modifier is indicative of a relative adjustment of the generic workload data representative of the workload of drivers when performing a given manoeuvre or traversing one or more segments, which may result in individual workload data for the corresponding manoeuvre or traversal of the one or more segments, e.g. a parameter that is adapted for the given individual. In general, the individual modifier may be representative of the workload for an individual driver when performing the manoeuvre or traversal of the segments relative to the generic workload indicated by the generic workload data based upon a workload of multiple drivers.

In embodiments, the modifier and/or data representative of the behaviour of the individual driver upon which it is based may or may not be specific to (the behaviour of the driver when) performing the manoeuvre at the node or traversing the one or more segments in respect to which the individual workload data is to be determined. Preferably the modifier and/or the data representative of the behaviour of the individual driver is not specific to performing the given manoeuvre or traversing the one or more segments. It will be appreciated that the present invention, by relying upon modifying generic workload data, avoids the need to generate individual driver workload data for specific manoeuvres or traversals of segments of an electronic map, instead providing a modifier which can be used to relatively adjust the generic workload data to provide individual workload data in respect of any of a plurality of different manoeuvres or traversals of segments. The modifier may be applicable to manoeuvres or the traversal of segments which the individual driver has not previously traveled.

The individual modifier may be based upon one or more aspects of the individual drivers behaviour. Where multiple aspects are taken into account, the modifier may be a function of the multiple aspects. The modifier may then be generated in any suitable manner, e.g. in a similar manner in which a weighting for a segment is obtained balancing various attributes when calculating a route. The individual modifier is preferably a single value. The individual modifier may be a normalised value. The individual modifier may be an individual modifier parameter.

The individual modifier may be based upon data indicative of one or more variables indicative of the drivers behaviour. In preferred embodiments the modifier is based, at least in part, on data automatically determined during driving by the individual driver. The method extends to the step of determining data indicative of the behaviour of the driver for use in determining the modifier, preferably automatically. The data may be determined using an in-vehicle system or systems as known in the art. For example, the data may be based on data obtained by one or more sensors, a navigation device, ADAS, etc. Preferably the data is based at least in part upon data determined automatically during driving by the individual driver by a navigation device or ADAS of the vehicle being driven. Suitable techniques for collecting such data are known in the art, and illustrated by any of the documents discussed in the "Background to the Invention" section above. The data may be data collected specifically for the purposes of the present invention, or may be stored data. For example, an ADAS or navigation device may collect and store data indicative of one or more aspects of a drivers behaviour which may then be used to generate the individual driver modifier of the present invention. Such information may be collected in order to create an individual driver modifier.

The individual modifier may be based upon data indicative of any variable or variables indicative of a drivers behaviour, and which may be indicative of workload. The individual modifier is based upon the driving behaviour of the driver, and hence the variable(s) relate to the driving behaviour of the driver. In preferred embodiments the individual modifier is representative of, and based upon data indicative of a driving style of the driver. The individual modifier may be representative of, and based upon data indicative of the acceleration, deceleration, curve aggression factor, speed or braking of the individual driver. Such variables are indicative of a driving behaviour or style of the driver. For example, the acceleration or braking patterns of the driver may indicate whether the driver is a smooth or erratic type of driver, or a level of aggression of the driver. This data may then enable the generic workload data to be appropriately modified for the individual. For example, workload values may be increased for erratic drivers, or decreased for smoother drivers. Such data may be collected using appropriate in-vehicle systems. It is envisaged that the driver modifier might be based upon data relating to the real-time behaviour of the driver, or may be based upon data collected relating to behaviour over a longer period e.g. one month, etc. It has been found that such data is relatively simple to obtain, and can provide a useful indicator of the drivers actual behaviour. This may be more accurate than relying upon, e.g. a drivers own assessment of their driving style.

In embodiments in which the generic driver workload data is based on the behaviour of multiple drivers, the data may be based on any of the variables discussed in relation to the individual driver behaviour, and may be collected in the same manner. The only difference is that it is then subjected to some processing to obtain average or generic behaviour. Unlike the individual driver behaviour, the behaviour used to obtain generic driver workload would typically relate to the behaviour of the drivers when performing the given manoeuvre or traversing the given segment(s).

The individual modifier may be representative of the driving style of the individual driver relative to an average behaviour. For example the individual modifier may indicate that the driver is relatively cautious, aggressive, etc. The modifier may be representative of a category of driving style satisfied by the individual driver.

The modifier may be generated for the purposes of determining particular individual user workload data. For example, the modifier may be determined on the fly when given user workload data is required, e.g. in relation to a calculated route in order to determine how to provide navigation instructions etc. However, in preferred embodiments the modifier is generated in advance.

In some embodiments the individual modifier is specific to a set of one or more environmental and/or temporal conditions. For example, the environmental conditions may include one or more of weather or lighting conditions. Temporal conditions may be for a given time of day, e.g. night time, day time, season, etc. In these embodiments the individual workload data obtained will similarly be specific to the set of one or more environmental and/or temporal conditions. In these embodiments the individual modifier may be obtained using data representative of the behaviour of the individual driver under the set of one or more environmental and/or temporal conditions. The method may comprise obtaining a first individual modifier indicative of the behaviour of an individual driver for use in determining individual driver workload data for a given manoeuvre or traversal of one or more segments specific to a first set of one or more environmental and/or temporal conditions, and one or more further individual modifier(s), and in embodiments, sets of individual workload data, specific to the further set of one or more environmental and/or temporal conditions. It will be appreciated that the generic driver workload data may or may not also be specific to a set of one or more environmental and/or temporal conditions. Preferably the generic driver workload data is indicative of the generic workload of drivers when performing the manoeuvre or traversing the set of one or more segments specific to a set of one or more environmental and/or temporal conditions.

In accordance with the invention, the data indicative of individual driver workload is obtained for at least one manoeuvre at a node or traversal of a set of one or more segments of an electronic map. The method may comprise generating a single individual modifier, or a plurality of individual modifiers representative of individual driver behaviour for use in obtaining individual driver workload data indicative of the individual driver workload when performing different manoeuvres at a node or nodes or traversing different sets of one or more segments of the electronic map. Each modifier where a plurality of modifiers are generated may be in accordance with any of the embodiments discussed above.

In a particularly simple embodiment, the method comprises generating a single individual modifier for use in determining an individual user workload data in respect of each manoeuvre at each node and each traversal of a set of one or more segments of the electronic map for which individual user workload data is to be determined.

As mentioned above, while a modifier may be generated in respect of each possible manoeuvre and/or traversal of a set of one or more segments of the electronic map for which individual driver workload data is required, preferably a limited set of modifiers is generated. One or a plurality of individual modifiers may be generated. Preferably the or each individual modifier may be, and preferably is used to obtain individual driver workload data indicative of the workload of the individual driver when performing any one of a plurality of different manoeuvres at a node or nodes and/or traversing any one of a plurality of sets of one or more segments of an electronic map. This may be achieved where the generic driver workload data forms part of a generic driver workload profile for different manoeuvres or segments of an electronic map as described above. Thus, the or each individual modifier generated in respect of obtaining individual driver workload data for a first manoeuvre at a node or traversal of a set of one or more segments of an electronic map is preferably used in respect of obtaining data indicative of an individual driver workload for at least one, and preferably a plurality of, further manoeuvre(s) at a node and/or the traversal of at least one, and preferably a plurality of further set(s) of one or more segments of an electronic map using generic driver workload data for the given manoeuvre and/or traversal of one or more segments.

In some embodiments of the invention the manoeuvre at a node or traversal of a set of one or more segments of an electronic map is a first manoeuvre at a node or traversal of a set of one or more segments of an electronic map, and the method further comprises obtaining data indicative of an individual driver workload for at least one, and preferably a plurality of, further manoeuvre(s) at a node and/or the traversal of at least one, and preferably a plurality of further set(s) of one or more segments of an electronic map, wherein the method comprises determining the individual driver workload data based on generic driver workload data for the at least one further manoeuvre at a node and/or the traversal of at least one further set of one or more segments of the electronic map using the individual modifier generated in relation to determining the individual driver workload data in respect of the first manoeuvre at a node or traversal of a set of one or more segments of an electronic map. In these embodiments, the method may comprise selecting the individual modifier, e.g. from a database of individual modifiers for use in determining the individual driver workload data in respect of the further manoeuvre or traversal of a set of one or more segments.

In some embodiments in which a plurality of individual modifiers are generated, a given individual modifier is used for determining the individual driver workload data in respect of a plurality of manoeuvres at a node or nodes, or a plurality of traversals of sets of one or more segments of an electronic map.

The plurality of manoeuvres or traversals of sets of one or more segments may be a plurality of manoeuvres or traversals of sets of one or more segments which manoeuvres or sets of one or more segments share one or more common attributes. In embodiments the method may comprise using an individual modifier generated in relation to determining individual driver workload data in respect of a first manoeuvre at a node or traversal of a set of one or more segments of an electronic map as the individual modifier for determining individual driver workload data in respect of at least one further manoeuvre at a node and/or the traversal of at least one further set of one or more segments of the electronic map which share one or more common attributes with the first manoeuvre at a node or traversal of a set of one or more segments. The individual modifier may be selected, e.g. from a database of modifiers, for use in the determination of the individual driver workload data based upon the attribute(s) of the manoeuvre or the set of one or more segments. The attributes may be objective attributes, e.g. a complexity, geometry or position of the node or segment(s), or a type of manoeuvre. For example, the attribute may be indicative of a left turn type manoeuvre, a segment including a tunnel, etc. Thus the attributes may be based on map data. However in other embodiments the one or more common attributes are determined by reference to the behaviour of the individual driver. In embodiments the manoeuvres or sets of one or more segments are ones which share some attribute which provokes a given type of driver behaviour. For example, an individual driver may experience particular difficulty when traversing segments having a left turn within a tunnel. These types of segment may then be associated with the same individual driver modifier. More or less complex criteria may be used to obtain a group of manoeuvres or sets of segments whose traversal may be described by a given individual modifier based upon driver behaviour. The particular conditions, e.g. environmental or temporal, might also be taken into account.

For example, a driver might experience difficulty with tunnel segments only at night and find the same segments relatively easy to traverse in the day.

In other embodiments the first manoeuvre at a node or traversal of a set of one or more segments of an electronic map and the at least one further manoeuvre at a node and/or the traversal of at least one further set of one or more segments of the electronic map are associated with a given predetermined route.

In some preferred embodiments a first individual modifier is generated for use in relation to performing manoeuvres or traversing segments forming part of a given predetermined route, and a second individual modifier is generated for use in relation to performing manoeuvres or traversing segments that do not form part of the predetermined route. In accordance with some embodiments, the manoeuvre at a node or the traversal of the set of one or more segments of an electronic map forms part of a first predetermined route, and the method further comprises obtaining data indicative of an individual driver workload for at least one, and preferably a plurality of, further manoeuvre(s) at a node and/or the traversal of at least one, and preferably a plurality of further set(s) of one or more segments of an electronic map which do not form part of the first predetermined route, wherein the method comprises generating a further individual modifier for use in determining the individual driver workload data based on generic driver workload data for the at least one further manoeuvre at a node and/or the traversal of at least one further set of one or more segments of the electronic map using the individual modifier, and preferably using the further individual modifier to determine the individual driver workload data based on the generic driver workload data. Preferably the predetermined route or first predetermined route, is a frequently traveled or favourite route of the driver. The route may be a pre-calculated route stored by a navigation device of the driver. In these embodiments the method may distinguish between predetermined routes, e.g. a favourite route, of the driver or a frequently traveled route, and other regions which may not form part of such a route. It may be determined that a lower workload is associated with favourite routes, due to their familiarity, with the individual modifier being selected appropriately to result in relative lower workload.

The individual driver workload data obtained in accordance with the invention in any of its aspects or embodiments is indicative of the workload of the individual driver when performing the manoeuvre at a node and/or traversing the one or more segments of an electronic map corresponding to the manoeuvre or the traversal of one or more segments upon which the generic driver workload data used with the individual modifier in determining the individual driver workload data is based. Preferably the individual driver workload data is an individual driver workload parameter.

The individual modifier may be used in any manner with the generic workload parameter to obtain an individual driver workload data for a manoeuvre or traversal of one or more segments. In embodiments the individual driver workload data, e.g. parameter, is a function of the individual driver modifier and the generic driver workload data, e.g. parameter, for performing the relevant manoeuvre or traversal of one or more segments. In some embodiments the individual driver workload data, e.g. parameter, is a product of the generic driver workload data, e.g. parameter, and the individual driver modifier. In embodiments the individual driver workload data is obtained relative to the generic driver workload data. In preferred embodiments, the individual and generic driver workload data and the modifier are normalised to facilitate calculation. Other factors may be taken into account when obtaining the individual workload data. For example, the data may involve a contribution based on factors such as driver age, or similar, which may not be reflected by the modifier based on driver behaviour.

In some embodiments, the method may comprise storing the individual driver workload data obtained in relation to a manoeuvre at a node or traversal of a set of one or more segments of the electronic map, and/or storing an individual modifier or modifiers obtained.

Individual driver workload data or an individual modifier may be stored in association with electronic map data, i.e. indicative of the manoeuvre or set of one or more segments to which it relates where applicable (an individual modifier may not be specific to particular manoeuvres or segments). The individual driver workload data may be stored alone, or as part of a profile indicative of individual driver workload for different manoeuvres or the traversal of different segments of an electronic map. In these embodiments, the workload data may be provided as a data layer associated with the map data. Individual driver workload data or an individual modifier may be stored in association with data indicative of the identity of the driver to which it relates. In embodiments in which an individual modifier relates to a given predetermined, e.g. favourite route, the method may comprise storing the modifier in association with data identifying the route.

It will be appreciated that an individual driver workload profile may be obtained using individual workload data for different manoeuvres and/or the traversal of different sets of segments of an electronic map in a similar manner to the generic driver workload profile described above. In some embodiments the method extends to obtaining such a profile.

In some embodiments the method comprises using individual driver workload data obtained in respect of different manoeuvres and/or the traversal of different sets of segments of the electronic map to provide an individual driver workload profile indicative of the workload of the individual driver when performing each of a plurality of different manoeuvres at a node or nodes and/or traversing a plurality of sets of one or more segments of the electronic map. The method may comprise storing the profile. The profile may be associated, and for example stored in association with, data indicative of the identity of the individual driver. In this way, a customised individual driver workload profile may be created.

In embodiments in which the generic driver data forms part of a generic driver workload profile including generic driver workload data in respect of a plurality of manoeuvres at a node or nodes and/or the traversal of a plurality of sets of one or more segments, the method may comprise using the or each individual modifier to create an individual driver workload profile including individual driver workload data in respect of the plurality of manoeuvres at a node or nodes and/or the traversal of the plurality of sets of one or more segments. In particularly simple embodiments in which the same modifier is used for any manoeuvre or traversal of one or more segments, the individual driver workload profile may be a function of the individual modifier and the generic driver workload profile. In embodiments in which an individual profile is derived, the individual modifier may not be stored. The individual driver profile may be stored in association with data indicative of the identity of the driver, and may then be used in place of the generic driver profile when workload is to be considered.

In some embodiments, the method may comprise storing data indicative of the or each individual modifier. However, it is envisaged that individual modifiers need not necessarily be stored, or at least may only be stored temporarily, where individual workload data obtained using the modifiers is stored. In some preferred embodiments the or each individual modifier is associated with data indicative of the identity of the driver to which it relates. In embodiments the or each individual modifier may be associated with data indicative of a manoeuvre at a node and/or set of one or more segments to which it relates. However, as discussed above, individual modifiers are preferably not derived for each set of segments or manoeuvre, and instead may be derived for a group of manoeuvre or set of segments sharing common attribute(s) or being associated with a given predetermined route. In some embodiments the or each individual modifier is associated with, and may be stored associated with, data indicative of an attribute or attributes of a manoeuvre at a node and/or set of one or more segments to which it is applicable, or alternatively the predetermined routes, to which it is applicable. This may enable the data to more readily be applied to other manoeuvres at a node or the traversal of segments which may be considered to have the same attribute(s). For example, the data may refer to a particular type of turn, or similar, based upon a suitable reference system.

In some embodiments the or each individual modifier obtained is stored, preferably in association with data indicative of the driver to which it relates. For example, the or each modifier may be stored in a modifier database in respect of a given individual driver.

In embodiments in which a single modifier is obtained in respect of a given individual driver, for use in respect of any manoeuvre or the traversal of any segment or segments, the method may comprise storing the individual modifier in association with information indicative of the identity of the driver. The information indicative of the identity of the driver may be directly or indirectly indicative of the identity of the driver. For example, the information may be indicative of a unique identifier of a navigation device of the driver etc. In embodiments the method may comprise determining the identity of a driver of a vehicle, and selecting the modifier in respect of the driver for use in obtaining individual driver workload data in respect of one or more given manoeuvre at a node and/or traversal of one or more segments. The driver identity may be determined automatically, e.g. by consideration of a navigation device identity, or may be confirmed or input by a user. In these embodiments, once a given driver is identified, the relevant modifier may be retrieved and used to obtain an individual driver workload profile based upon a generic driver workload profile. These steps may be carried out by an in-vehicle system, e.g. navigation device. The step of generating the modifier may be carried out by a server, such that the navigation device might then obtain the modifier for use in a given situation from the server, and then use it to obtain an individual workload profile.

In some embodiments an individual modifier may be determined in real time, or approximately real time. This could be carried out by a navigation device or other in-vehicle system, or by a server and then transmitted to an in-vehicle system.

In general, it will be appreciated that an individual modifier may be generated, or at least selected and used to obtain individual driver workload data, as required, e.g. by an in-vehicle system such as a navigation device or ADAS. In other arrangements, individual driver workload data may be obtained in advance, e.g. by obtaining an individual workload profile for a given driver using the individual modifier(s) relevant for a given area. This could be carried out by a server with an in-vehicle device then being provided with the profile rather than individual modifiers.

In accordance with some embodiments the method comprises identifying a manoeuvre at a node or a traversal of one or more segments that is to be performed along a route being or to be navigated by a driver, and determining an individual modifier representative of the behaviour of the driver for use in obtaining individual driver workload data for the manoeuvre or the traversal of the one or more segments. The step of determining the individual modifier may be carried out in any of the manners described herein. The step may comprise generating the modifier, or identifying one or more attributes of the node or manoeuvre or the one or more segments and selecting an individual modifier based on the attribute or attributes, or selecting an individual modifier based on the predetermined route.

The present invention extends to the use of the individual workload data in controlling the operation of an in-vehicle system. The step of controlling operation may comprise controlling the communication of the in-vehicle system with the driver, disabling or enabling one or more functions of the system, causing the system to provide a warning or alert to a driver, or causing the system to enhance an electronic map displayed to the user. Controlling communication with a driver may comprise modifying the density or type of navigation instructions provided, the presentation of navigation information, etc. Examples of functions enabled or disabled may include non-driving related functions, e.g. a phone function. Examples of ways in which individual workload data may be used to control the operation of an in-vehicle system are known in the art, and described in the documents referred to above. The method may comprise controlling the operation of the in-vehicle system to modify the driver workload demanded by the system depending upon the individual workload required, e.g. to perform a given manoeuvre or traverse one or more segments. Thus, where workload of the driver is expected to be relatively low, the system may be controlled to allow it to demand a greater amount of workload, whereas when driver workload is expected to be high, the workload required by the system may be reduced. The in-vehicle system may be a navigation device, e.g. PND or integrated device, or an ADAS. The method may comprise controlling the operation of the in-vehicle system using the individual workload data during or prior to the driver traversing the one or more segments or performing the manoeuvre at the node to which the parameter relates. The method may comprise calculating a route taking into account the individual workload data, e.g. to minimise individual workload. The method may comprise displaying information regarding individual workload to a driver. Information may be displayed regarding individual workload for different manoeuvres or segments of an electronic map.

It will be appreciated that where generic driver workload data, or equally individual driver workload data relates to the traversal of a plurality of segments, this may be indicative of the generic or individual driver workload as appropriate when traversing the segments including carrying out any given manoeuvre or other action at a node or nodes between the segments that is required to traverse the segments. For example, the workload for traversing a plurality of segments may be indicative of the workload when performing a set of manoeuvres at one or more nodes between a segment or segments of the electronic map. Thus, the workload may be indicative of a driver workload when performing a so called "complex manoeuvre".

An electronic map as referred to herein comprises a plurality of nodes connected by a plurality of segments, the segments being indicative of navigable segments. The navigable segment(s) referred to herein are segment(s) in an area covered by an electronic map. While exemplary embodiments refer to road segments of a road network, it will be appreciated that the invention is applicable to any form of navigable segment, including segments of a path, river, canal, cycle path, tow path, railway line, or the like. For ease of reference these are commonly referred to as a road segment of a road network. In accordance with the invention, the method may be carried out in respect of obtaining individual driver workload data in respect of one or manoeuvre at a node or nodes, and/or the traversal of one or more sets of one or more segments of an electronic map. If not explicitly stated, where a plurality of manoeuvres are considered, these may be a plurality of manoeuvres at the same node, and/or manoeuvres at two or more different nodes of an electronic map. The same applies in respect of generic driver workload data.

The present invention extends to a data product storing individual driver workload data indicative obtained in accordance with the method of the present invention in any of its aspects or embodiments. The data product in any of these further aspects or embodiments of the invention, may be of any suitable form. In some embodiments the data product may be stored on a computer readable medium. The computer readable medium may be, for example, a diskette, CD ROM, ROM, RAM, flash memory or hard disk. The present invention extends to a computer readable medium comprising the data product in accordance with the invention of any of its aspects or embodiments.

While the present invention has been described with particular reference to obtaining individual workload data, it is envisaged that in accordance with certain broader aspects, similar techniques may be applied to obtaining data in respect of other aspects of an individual drivers driving when performing a manoeuvre at a node or traversing a set of one or more segments of an electronic map using generic driver data for the corresponding aspect of driving.

In accordance with a further aspect of the invention there is provided a method of determining data relating to an aspect of the driving of an individual driver when performing a manoeuvre at a node or traversing a set of one or more segments of an electronic map, the method comprising:

obtaining generic driving data representative of the driving aspect when performing a manoeuvre at a node or traversing a set of one or more segments of an electronic map;

generating an individual modifier representative of the behaviour of an individual driver for use in determining individual driver data indicative of the aspect of driving of the individual driver when performing the manoeuvre at the node or traversing the one or more segments of an electronic map based on the generic driver data for performing the manoeuvre at the node or traversing the one or more segments of the electronic map; and, optionally, using the individual modifier to determine individual driver data indicative of the aspect of driving of the individual driver when performing the manoeuvre at the node or traversing the one or more segments of the electronic map based on the generic driver data for the manoeuvre at the node or the traversal of the one or more segments.

The driving aspect may be a speed of travel, acceleration, etc. In embodiments, wherein the driving aspect is the speed of travel, the individual driver data, i.e. the expected speed of travel of the driver's vehicle, which may be slower or faster than the average speed, may be used to adjust: the estimated time of arrival (ETA), e.g. increase for slow drivers; the threshold for warning when speeding, e.g. raise for fast drivers; the timing of (voice) navigation instructions/warnings, e.g. earlier for fast drivers; the type of (voice) instruction, e.g. less information for fast drivers; the zoom level of the driving view, e.g. more zoomed for slow drivers; the type of route, e.g. slow drivers get the most economical (or "green") route.

The present invention in this further aspect may include any of the features described in relation to the earlier aspects of the invention to the extent they are not mutually inconsistent therewith. Thus, any reference to "workload" may be replaced with a reference to any other specific aspect of driving, or, an aspect of driving in general.

References herein to data being associated with, for example, other data, should not be interpreted to require any particular restriction on data storage locations. The phrase only requires that the features are identifiably related to an intersection. Therefore association may for example be achieved by means of a reference to a side file, potentially located in a remote server.

Embodiments of the method may be performed by an offline navigation device. In this way a navigation device not connected to a communication network may still employ embodiments of the invention.

Any of the methods in accordance with the present invention may be implemented at least partially using software, e.g. computer programs. The present invention thus also extends to a computer program comprising computer readable instructions executable to perform a method according to any of the aspects or embodiments of the invention.

The invention correspondingly extends to a computer software carrier comprising such software which when used to operate a system or apparatus comprising data processing means causes in conjunction with said data processing means said apparatus or system to carry out the steps of the methods of the present invention. Such a computer software carrier could be a non-transitory physical storage medium such as a ROM chip, CD ROM or disk, or could be a signal such as an electronic signal over wires, an optical signal or a radio signal such as to a satellite or the like.

Where not explicitly stated, it will be appreciated that the invention in any of its aspects may include any or all of the features described in respect of other aspects or embodiments of the invention to the extent they are not mutually exclusive. In particular, while various embodiments of operations have been described which may be performed in the method and by the system or apparatus, it will be appreciated that any one or more or all of these operations may be performed in the method and by the system or apparatus, in any combination, as desired, and as appropriate.

Advantages of these embodiments are set out hereafter, and further details and features of each of these embodiments are defined in the accompanying dependent claims and elsewhere in the following detailed description.

BRIEF DESCRIPTION OF THE DRAWINGS

Some preferred embodiments of the invention will now be described by way of example only, and with reference to the accompanying figures of which.

DETAILED DESCRIPTION OF PREFERRED EMBODIMENTS

Preferred embodiments of the present invention will now be described with particular reference to a PND. It should be remembered, however, that the teachings of the present invention are not limited to PNDs but are instead universally applicable to any type of processing device that is configured to execute navigation software so as to provide navigation functionality. It follows therefore that in the context of the present application, a navigation device is intended to include (without limitation) any type of navigation device, irrespective of whether that device is embodied as a PND, a navigation device built into a vehicle, or indeed a computing resource (such as a desktop or portable personal computer (PC), mobile telephone or portable digital assistant (PDA)) executing navigation software. In addition, the present invention is applicable to devices with the ability to obtain position data for the device, but which may not provide navigation or route planning functionality. For example, such a device could be located in a vehicle, and arranged to provide speed recommendations via an instrument panel of the vehicle, obtaining position data from the vehicle or a position determining, e.g. GPS system of the device itself.

Figure 1:
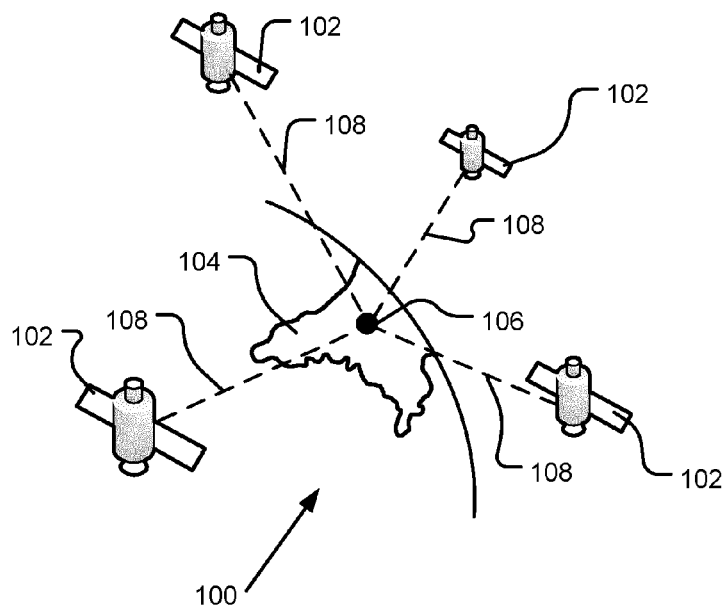
FIG. 1 is a schematic illustration of a Global Positioning System (GPS)

With the above provisos in mind, FIG. 1 illustrates an example view of Global Positioning System (GPS), usable by navigation devices. Such systems are known and are used for a variety of purposes. In general, GPS is a satellite-radio based navigation system capable of determining continuous position, velocity, time, and in some instances direction information for an unlimited number of users. Formerly known as NAVSTAR, the GPS incorporates a plurality of satellites which orbit the earth in extremely precise orbits. Based on these precise orbits, GPS satellites can relay their location to any number of receiving units.

The GPS system is implemented when a device, specially equipped to receive GPS data, begins scanning radio frequencies for GPS satellite signals. Upon receiving a radio signal from a GPS satellite, the device determines the precise location of that satellite via one of a plurality of different conventional methods. The device will continue scanning, in most instances, for signals until it has acquired at least three different satellite signals (noting that position is not normally, but can be determined, with only two signals using other triangulation techniques). Implementing geometric triangulation, the receiver utilizes the three known positions to determine its own two-dimensional position relative to the satellites. This can be done in a known manner. Additionally, acquiring a fourth satellite signal will allow the receiving device to calculate its three dimensional position by the same geometrical calculation in a known manner. The position and velocity data can be updated in real time on a continuous basis by an unlimited number of users.

As shown in FIG. 1, the GPS system is denoted generally by reference numeral 100. A plurality of satellites 120 are in orbit about the earth 124. The orbit of each satellite 120 is not necessarily synchronous with the orbits of other satellites 120 and, in fact, is likely asynchronous. A GPS receiver 140 is shown receiving spread spectrum GPS satellite signals 160 from the various satellites 120.

The spread spectrum signals 160, continuously transmitted from each satellite 120, utilize a highly accurate frequency standard accomplished with an extremely accurate atomic clock. Each satellite 120, as part of its data signal transmission 160, transmits a data stream indicative of that particular satellite 120. It is appreciated by those skilled in the relevant art that the GPS receiver device 140 generally acquires spread spectrum GPS satellite signals 160 from at least three satellites 120 for the GPS receiver device 140 to calculate its two-dimensional position by triangulation. Acquisition of an additional signal, resulting in signals 160 from a total of four satellites 120, permits the GPS receiver device 140 to calculate its three-dimensional position in a known manner.

Figure 2:
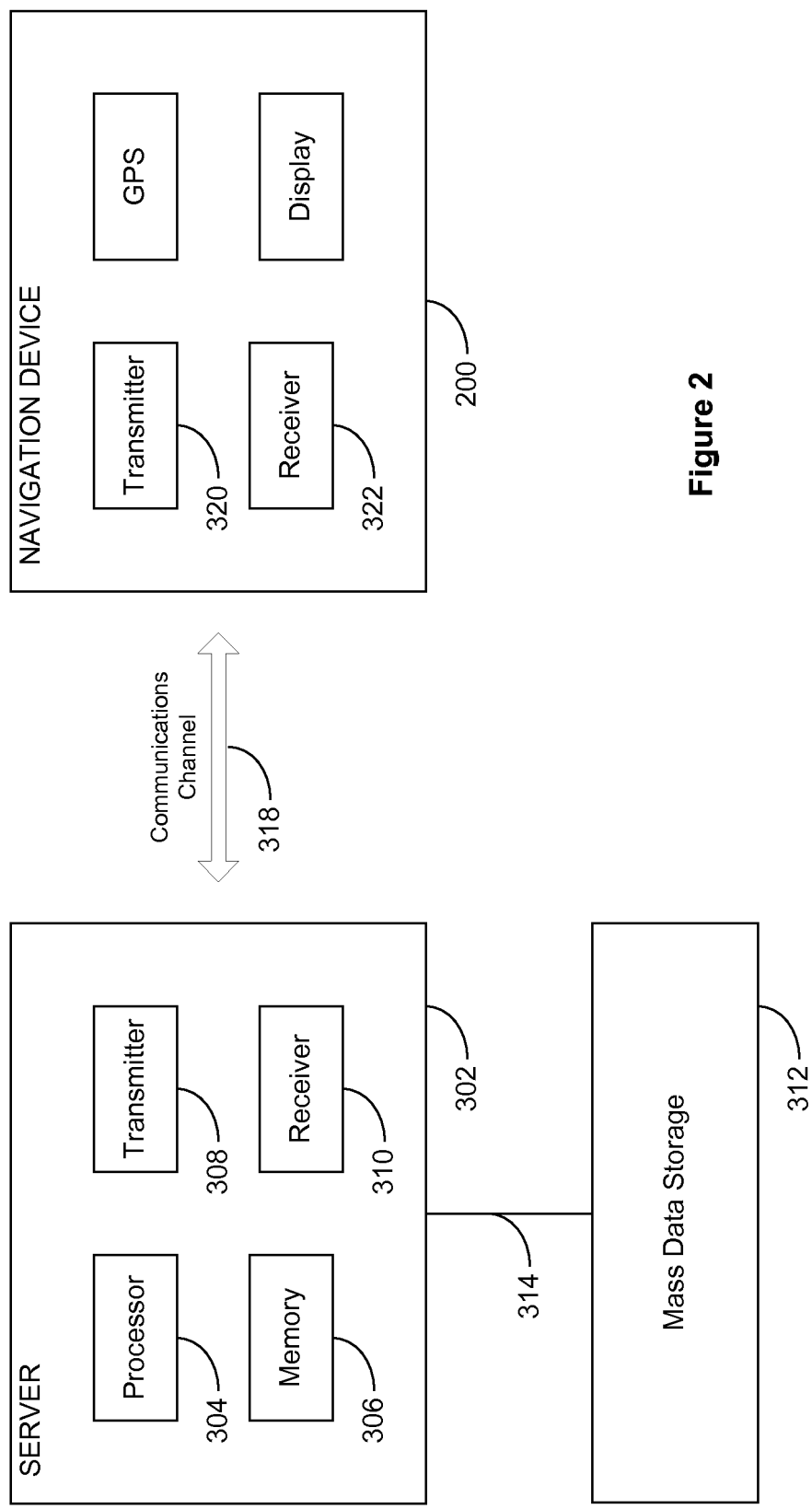
FIG. 2 is a schematic illustration of electronic components arranged to provide a navigation device.

FIG. 2 is an illustrative representation of electronic components of a navigation device 200 usable according to a preferred embodiment of the present invention, in block component format. It should be noted that the block diagram of the navigation device 200 is not inclusive of all components of the navigation device, but is only representative of many example components.

The navigation device 200 is located within a housing (not shown). The housing includes a processor 210 connected to an input device 220 and a display screen 240. The input device 220 can include a keyboard device, voice input device, touch panel and/or any other known input device utilised to input information; and the display screen 240 can include any type of display screen such as an LCD display, for example. In a particularly preferred arrangement the input device 220 and display screen 240 are integrated into an integrated input and display device, including a touchpad or touchscreen input so that a user need only touch a portion of the display screen 240 to select one of a plurality of display choices or to activate one of a plurality of virtual buttons.

The navigation device may include an output device 260, for example an audible output device (e.g. a loudspeaker). As output device 260 can produce audible information for a user of the navigation device 200, it is should equally be understood that input device 240 can include a microphone and software for receiving input voice commands as well.

In the navigation device 200, processor 210 is operatively connected to and set to receive input information from input device 220 via a connection 225, and operatively connected to at least one of display screen 240 and output device 260, via output connections 245, to output information thereto. Further, the processor 210 is operably coupled to a memory resource 230 via connection 235 and is further adapted to receive/send information from/to input/output (I/O) ports 270 via connection 275, wherein the I/O port 270 is connectible to an I/O device 280 external to the navigation device 200. The memory resource 230 comprises, for example, a volatile memory, such as a Random Access Memory (RAM) and a non-volatile memory, for example a digital memory, such as a flash memory. The external I/O device 280 may include, but is not limited to an external listening device such as an earpiece for example. The connection to I/O device 280 can further be a wired or wireless connection to any other external device such as a car stereo unit for hands-free operation and/or for voice activated operation for example, for connection to an ear piece or head phones, and/or for connection to a mobile phone for example, wherein the mobile phone connection may be used to establish a data connection between the navigation device 200 and the internet or any other network for example, and/or to establish a connection to a server via the internet or some other network for example.

FIG. 2 further illustrates an operative connection between the processor 210 and an antenna/receiver 250 via connection 255, wherein the antenna/receiver 250 can be a GPS antenna/receiver for example. It will be understood that the antenna and receiver designated by reference numeral 250 are combined schematically for illustration, but that the antenna and receiver may be separately located components, and that the antenna may be a GPS patch antenna or helical antenna for example.

Further, it will be understood by one of ordinary skill in the art that the electronic components shown in FIG. 2 are powered by power sources (not shown) in a conventional manner. As will be understood by one of ordinary skill in the art, different configurations of the components shown in FIG. 2 are considered to be within the scope of the present application. For example, the components shown in FIG. 2 may be in communication with one another via wired and/or wireless connections and the like. Thus, the scope of the navigation device 200 of the present application includes a portable or handheld navigation device 200.

In addition, the portable or handheld navigation device 200 of FIG. 2 can be connected or "docked" in a known manner to a vehicle such as a bicycle, a motorbike, a car or a boat for example. Such a navigation device 200 is then removable from the docked location for portable or handheld navigation use.

Figure 3:
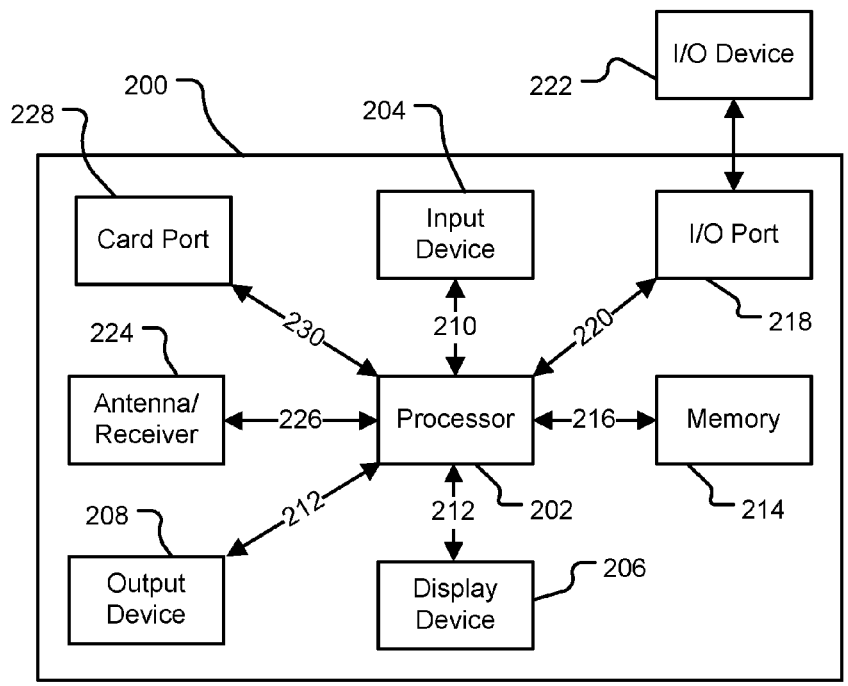
FIG. 3 is a schematic illustration of the manner in which a navigation device may receive information over a wireless communication channel.

Referring now to FIG. 3, the navigation device 200 may establish a "mobile" or telecommunications network connection with a server 302 via a mobile device (not shown) (such as a mobile phone, PDA, and/or any device with mobile phone technology) establishing a digital connection (such as a digital connection via known Bluetooth technology for example). Thereafter, through its network service provider, the mobile device can establish a network connection (through the internet for example) with a server 302. As such, a "mobile" network connection is established between the navigation device 200 (which can be, and often times is mobile as it travels alone and/or in a vehicle) and the server 302 to provide a "real-time" or at least very "up to date" gateway for information.

The establishing of the network connection between the mobile device (via a service provider) and another device such as the server 302, using an internet (such as the World Wide Web) for example, can be done in a known manner. This can include use of TCP/IP layered protocol for example. The mobile device can utilize any number of communication standards such as CDMA, GSM, WAN, etc.

As such, an internet connection may be utilised which is achieved via data connection, via a mobile phone or mobile phone technology within the navigation device 200 for example. For this connection, an internet connection between the server 302 and the navigation device 200 is established. This can be done, for example, through a mobile phone or other mobile device and a GPRS (General Packet Radio Service)-connection (GPRS connection is a high-speed data connection for mobile devices provided by telecom operators; GPRS is a method to connect to the internet).

The navigation device 200 can further complete a data connection with the mobile device, and eventually with the internet and server 302, via existing Bluetooth technology for example, in a known manner, wherein the data protocol can utilize any number of standards, such as the GPRS, the Data Protocol Standard for the GSM standard, for example.

The navigation device 200 may include its own mobile phone technology within the navigation device 200 itself (including an antenna for example, or optionally using the internal antenna of the navigation device 200). The mobile phone technology within the navigation device 200 can include internal components as specified above, and/or can include an insertable card (e.g. Subscriber Identity Module or SIM card), complete with necessary mobile phone technology and/or an antenna for example. As such, mobile phone technology within the navigation device 200 can similarly establish a network connection between the navigation device 200 and the server 302, via the internet for example, in a manner similar to that of any mobile device.

For GPRS phone settings, a Bluetooth enabled navigation device may be used to correctly work with the ever changing spectrum of mobile phone models, manufacturers, etc., model/manufacturer specific settings may be stored on the navigation device 200 for example. The data stored for this information can be updated.

In FIG. 3 the navigation device 200 is depicted as being in communication with the server 302 via a generic communications channel 318 that can be implemented by any of a number of different arrangements. The server 302 and a navigation device 200 can communicate when a connection via communications channel 318 is established between the server 302 and the navigation device 200 (noting that such a connection can be a data connection via mobile device, a direct connection via personal computer via the internet, etc.).

The server 302 includes, in addition to other components which may not be illustrated, a processor 304 operatively connected to a memory 306 and further operatively connected, via a wired or wireless connection 314, to a mass data storage device 312. The processor 304 is further operatively connected to transmitter 308 and receiver 310, to transmit and send information to and from navigation device 200 via communications channel 318. The signals sent and received may include data, communication, and/or other propagated signals. The transmitter 308 and receiver 310 may be selected or designed according to the communications requirement and communication technology used in the communication design for the navigation system 200. Further, it should be noted that the functions of transmitter 308 and receiver 310 may be combined into a signal transceiver.

Server 302 is further connected to (or includes) a mass storage device 312, noting that the mass storage device 312 may be coupled to the server 302 via communication link 314. The mass storage device 312 contains a store of navigation data and map information, and can again be a separate device from the server 302 or can be incorporated into the server 302.

The navigation device 200 is adapted to communicate with the server 302 through communications channel 318, and includes processor, memory, etc. as previously described with regard to FIG. 2, as well as transmitter 320 and receiver 322 to send and receive signals and/or data through the communications channel 318, noting that these devices can further be used to communicate with devices other than server 302. Further, the transmitter 320 and receiver 322 are selected or designed according to communication requirements and communication technology used in the communication design for the navigation device 200 and the functions of the transmitter 320 and receiver 322 may be combined into a single transceiver.

Software stored in server memory 306 provides instructions for the processor 304 and allows the server 302 to provide services to the navigation device 200. One service provided by the server 302 involves processing requests from the navigation device 200 and transmitting navigation data from the mass data storage 312 to the navigation device 200. Another service provided by the server 302 includes processing the navigation data using various algorithms for a desired application and sending the results of these calculations to the navigation device 200.

The communication channel 318 generically represents the propagating medium or path that connects the navigation device 200 and the server 302. Both the server 302 and navigation device 200 include a transmitter for transmitting data through the communication channel and a receiver for receiving data that has been transmitted through the communication channel.

The communication channel 318 is not limited to a particular communication technology. Additionally, the communication channel 318 is not limited to a single communication technology; that is, the channel 318 may include several communication links that use a variety of technology. For example, the communication channel 318 can be adapted to provide a path for electrical, optical, and/or electromagnetic communications, etc. As such, the communication channel 318 includes, but is not limited to, one or a combination of the following: electric circuits, electrical conductors such as wires and coaxial cables, fibre optic cables, converters, radio-frequency (RF) waves, the atmosphere, empty space, etc. Furthermore, the communication channel 318 can include intermediate devices such as routers, repeaters, buffers, transmitters, and receivers, for example.

In one illustrative arrangement, the communication channel 318 includes telephone and computer networks. Furthermore, the communication channel 318 may be capable of accommodating wireless communication such as radio frequency, microwave frequency, infrared communication, etc. Additionally, the communication channel 318 can accommodate satellite communication.

The communication signals transmitted through the communication channel 318 include, but are not limited to, signals as may be required or desired for given communication technology. For example, the signals may be adapted to be used in cellular communication technology such as Time Division Multiple Access (TDMA), Frequency Division Multiple Access (FDMA), Code Division Multiple Access (CDMA), Global System for Mobile Communications (GSM), etc. Both digital and analogue signals can be transmitted through the communication channel 318. These signals may be modulated, encrypted and/or compressed signals as may be desirable for the communication technology.

The server 302 includes a remote server accessible by the navigation device 200 via a wireless channel. The server 302 may include a network server located on a local area network (LAN), wide area network (WAN), virtual private network (VPN), etc.

The server 302 may include a personal computer such as a desktop or laptop computer, and the communication channel 318 may be a cable connected between the personal computer and the navigation device 200. Alternatively, a personal computer may be connected between the navigation device 200 and the server 302 to establish an internet connection between the server 302 and the navigation device 200. Alternatively, a mobile telephone or other handheld device may establish a wireless connection to the internet, for connecting the navigation device 200 to the server 302 via the internet.

The navigation device 200 may be provided with information from the server 302 via information downloads which may be periodically updated automatically or upon a user connecting navigation device 200 to the server 302 and/or may be more dynamic upon a more constant or frequent connection being made between the server 302 and navigation device 200 via a wireless mobile connection device and TCP/IP connection for example. For many dynamic calculations, the processor 304 in the server 302 may be used to handle the bulk of the processing needs, however, processor 210 of navigation device 200 can also handle much processing and calculation, oftentimes independent of a connection to a server 302.

As indicated above in FIG. 2, a navigation device 200 includes a processor 210, an input device 220, and a display screen 240. The input device 220 and display screen 240 are integrated into an integrated input and display device to enable both input of information (via direct input, menu selection, etc.) and display of information through a touch panel screen, for example. Such a screen may be a touch input LCD screen, for example, as is well known to those of ordinary skill in the art. Further, the navigation device 200 can also include any additional input device 220 and/or any additional output device 241, such as audio input/output devices for example.

Figure 4:
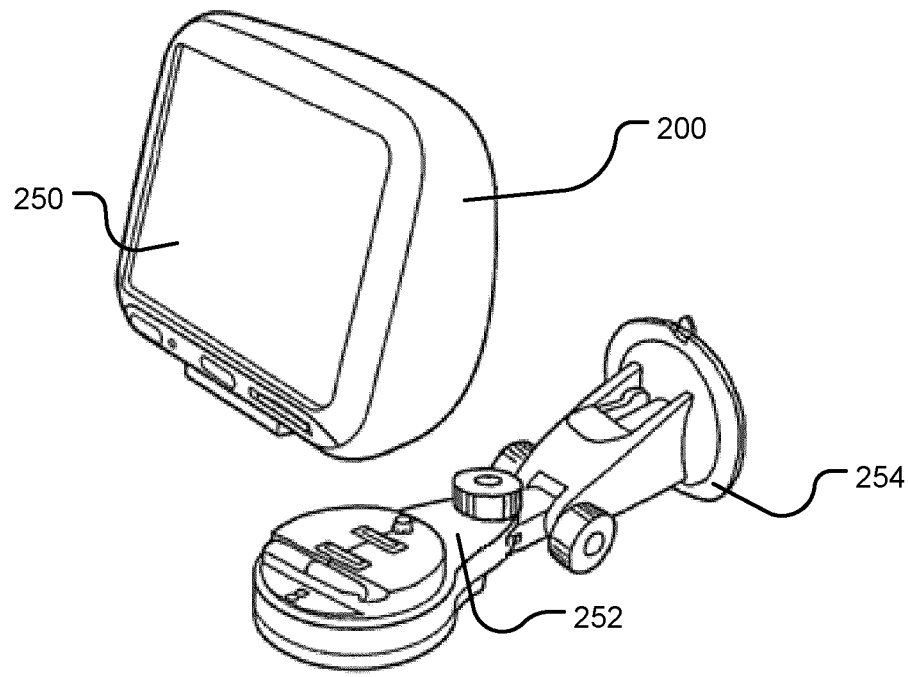
FIG. 4 is an illustrative perspective view of a navigation device.
Figure 5:
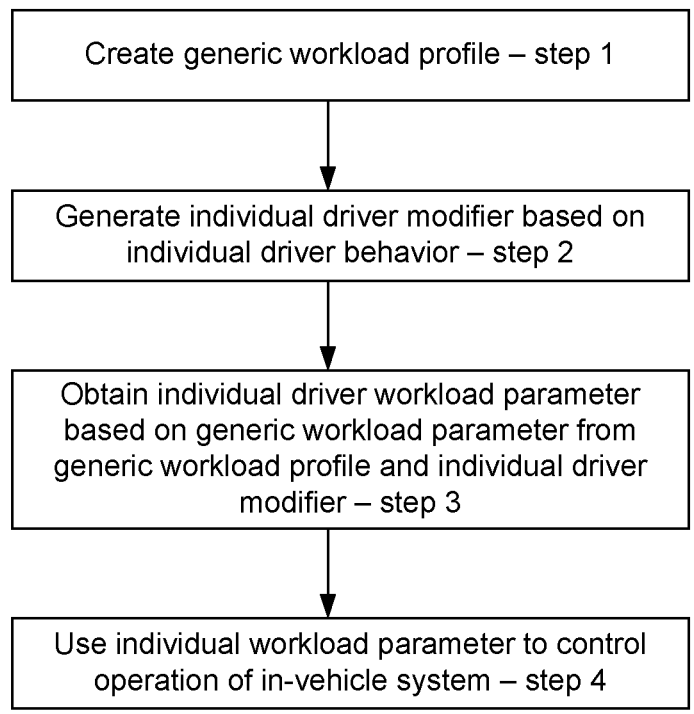
FIG. 5 is a flow chart illustrating one exemplary embodiment of the invention.

FIG. 4 is a perspective view of a navigation device 200. As shown in FIG. 4, the navigation device 200 may be a unit that includes an integrated input and display device 290 (a touch panel screen for example) and the other components of FIG. 2 (including but not limited to internal GPS receiver 250, microprocessor 210, a power supply, memory systems 230, etc.). The navigation device 200 may sit on an arm 292, which itself may be secured to a vehicle dashboard/window/etc. using a suction cup 294. This arm 292 is one example of a docking station to which the navigation device 200 can be docked. The navigation device 200 can be docked or otherwise connected to an arm 292 of the docking station by snap connecting the navigation device 292 to the arm 292 for example. The navigation device 200 may then be rotatable on the arm 292. To release the connection between the navigation device 200 and the docking station, a button on the navigation device 200 may be pressed, for example. Other equally suitable arrangements for coupling and decoupling the navigation device to a docking station are well known to persons of ordinary skill in the art.

FIGS. 1 to 4 are provided by way of background, illustrating certain features of navigation apparatus which may be used to implement methods of the present invention.

Before describing some preferred embodiments of the invention, we will first describe some detailed background to the invention.

The concept of a driver (mental) workload is well established, and efforts are made to take this into account when designing in-vehicle systems, such as navigation devices or ADAS systems. Driver mental workload ("workload") refers to the demand placed on the mental capacity of a driver in order to carry out the necessary tasks at a given time in a vehicle. Naturally, a primary task is that of driving. In addition, other systems in a vehicle may place further demands on the driver, using further mental capacity. For example, demands may be placed on the mental capacity of a driver by a personal navigation device (PND), when issuing route instructions, or indeed other peripheral devices, such as a telephone system or audio system of the vehicle.

Any driver will have a certain mental capacity, which may depend on various factors, such as age, and it is important to ensure that the drivers mental workload at any given time does not involve too great a proportion of his mental capacity, as this may have an adverse effect on driving performance, and ultimately safety. The mental workload of a driver will depend upon the individual and the task or tasks he or she is required to perform at any time. For example, one driver might find a particular left turn to be undemanding, while for another driver this may place a significant demand on the drivers mental capacity, being associated with a high mental workload for that driver. Navigating one section of road might impose a quite different mental workload on a driver than navigating another section of road. The workload of a driver when performing a given task may vary for a variety of reasons. For example, any workload of a driver may be affected by environmental factors, such as weather, visibility, lighting (e.g. whether day or night), traffic conditions. While it may not be possible to easily change the workload required in order to perform the main task of driving, the workload demanded by other in-vehicle systems can more easily be controlled, in order to try to maintain overall workload at a reasonable level within the mental capacity of the driver at any given time.

It is known to measure a drivers workload in various manners, and adapt the operation of an in-vehicle system depending on a drivers workload at any given time. Examples of such adaptations are found in, for example, US 2007/0124027 A1, US 2005/0234617 A1, and US 2006/0015219 A1, which are mentioned above.

Determination of driver mental workload may be carried out in various ways, and may be based upon information obtained from a variety of sources. For example, driver workload information might be based on information submitted by a user in response to questions, e.g. a driver profile questionnaire. Such a profile questionnaire might contain questions relating for example to the age of the driver, year that the driver obtained a license, driving style, according to a drivers stress inventory, personality questions, etc. Relevant information might be gathered, e.g. from a personal navigation device (PND), based on information already submitted by a user. Other relevant information might be gathered from a computer account of the user associated with the navigation device. Information entered via a PND or computer account associated with a PND might include information such as a brand or model of car, weight or size. Such information gives some indication of the character of a driver and their likely driving style etc., allowing a determination as to how their mental workload might compare to that of other drivers.

Workload of a driver may also be determined as a function of characteristic detected regarding a psychological or physiological state of a driver. For example, sensors in a vehicle may detect psychological data such as a galvanic skin response or other parameters, which might be considered indicative of the stress, and hence workload, being experienced by a user. Other sensors might determine external or internal environmental conditions which may affect workload, e.g. lighting, noise levels or other conditions inside the vehicle.

Information regarding mental workload may also be gathered from the actual driving behaviour of a user. This might be based on real time or historic driving behaviour of the individual. The present invention utilises such information. Information regarding actual driving behaviour of a user may be determined automatically based on detecting acceleration or braking behaviour of the driver, speed of travel, curve aggression factors, etc. Data may be sensed by specific sensors of a vehicle, by a navigation device, or an ADAS system, etc.

Systems for collecting data regarding driver behaviour are known. For example, one system is described in WO 2008/004857, in which a driver recorder detects so-called driving behaviour parameters reflecting a driving behaviour of the driver. The driver recorder may be provided as part of a navigation device, whether an integrated navigation device or PND associated with the vehicle, or may be are provided by separate in-vehicle systems, such as an ADAS.

As well as determining an individual driver workload, systems have also been proposed for determining some form of generic driver workload profile based on the behaviour of multiple drivers in respect of different regions of an electronic map. The creation of such generic driver workload profiles is envisaged, for example in WO 2009/0143903 A1, which describes a profile illustrating a variation in driver workload throughout a road network. Such a profile may be provided by obtaining generic driver workload parameters associated respectively with elements of an electronic map to which they relate. For example, parameters may be associated with traversing certain segments of the electronic map, or performing certain manoeuvres. Such a profile may be stored as a generic workload map layer, i.e. as a data layer associated with the map data. A map layer of this type may be obtained by consideration of various parameters indicative of workload as described above in respect of individual drivers. These can be used to create an average value for carrying out particular manoeuvres or traversing particular segments, or sequences of segments of an electronic map.

The Applicant has realised that conventional methods as described in the prior art do not address the need to be able to efficiently obtain data indicative of an individual driver workload. For example, a generic workload map layer does not take individual driver behaviour into account. As mentioned above, a particular manoeuvre might be difficult for one driver but not another, such that an individual drivers workload might not conform to an expected "average" workload based on a generic profile. Thus, relying upon generic workload data, being an average based on the workload of multiple drivers, may lead to inappropriate or inadequate action being taken in respect of an individual driver when the workload data is used to control an in-vehicle system. This may result in the driver feeling that the system is not taking into account workload in its operation, and the system failing to adequately support the driver.

While individual workload data may be collected, and used to provide an individual workload profile, e.g. as proposed in WO 2009/143903 A1, obtaining the necessary data, and processing it in respect of an individual can be time consuming and complex. It may take some time to collect a meaningful amount of data about a given driver, particularly when a driver does not travel frequently, or in a variety of different areas.

The present invention provides an improved method for obtaining individual driver workload data.

A preferred embodiment of the invention will now be described.

In accordance with a first step of a method in accordance with the invention, a generic driver workload parameter is obtained. This parameter is representative of a generic driver workload when performing a given manoeuvre at a node, or traversing one or more segments of an electronic map. The generic driver workload parameter may be based on theoretical workload models. For example, generic driver workload data might be obtained by consideration of map data. This might be done by consideration of the geometry of road segments, e.g. a level of curvature of a road segment, etc. However, in the preferred embodiments described herein, the generic driver workload parameter is based on actual detected driving behaviour of multiple drivers when performing the manoeuvre or traversing the one or more segments. Examples of such detected behaviour are found in the prior art discussed above, and are further discussed in relation to determining individual driver workload below.

The generic driver workload parameter is in the form of a numerical value associated with the map data indicative of the relevant node or one or more segments of the map. Where the workload parameter refers to a manoeuvre at a node, it is also associated with information indicative of the particular manoeuvre at the node. The generic driver workload parameter is associated with performing either a manoeuvre at a node, or alternatively traversing one or more segments of an electronic map. In the latter case, it will be appreciated that the generic workload parameter may be indicative of the generic workload for performing a complex manoeuvre or any sequence of manoeuvres involved in traversing the one or more segments. For example, where a user has to traverse two or more segments, the workload parameter may be indicative of the workload involved in travelling from one end of the stretch defined by the segments to the other, including performing a manoeuvre at a roundabout connecting the segments.

The generic driver workload parameter forms part of a generic driver workload profile, indicative of workload parameters for different manoeuvres or traversals of sets of one or more segments of an electronic map. The way in which a generic driver workload profile is obtained will not be described in detail. Methods of determining generic workload profiles are described for example in WO 2009/143903. The generic driver workload profile is indicative of the variation of driver workload associated with performing different manoeuvres or the traversal of different sets of segments over the geographic region represented by the electronic map. The generic driver workload profile may be of any type which provides an indication of the relative complexity, and hence workload associated with performing different manoeuvres, or traversing different segments of an electronic map.

It is envisaged that the generic driver workload parameter may be obtained from an existing generic driver workload profile, and that obtaining the parameter may therefore comprise selecting the relevant stored parameter from a generic driver workload database. In other arrangements, the method may extend to creating a generic driver workload profile from which the parameter may be obtained. This may be carried out by means of a server using data transmitted thereto e.g. being indicative of the behaviour of different drivers. The data may be transmitted to the server via navigation devices or ADAS of vehicles of the different drivers. The workload data is time stamped and associated with position data, enabling generic workload parameters indicative of an average driver workload to be derived for different manoeuvres or positions of the electronic map. The data used to determine workload may be indicative of a driver behaviour, e.g. acceleration, deceleration, speed, curve aggression, speed of travel, etc, which may be indicative of driver workload. A map matched workload map layer based on data obtained regarding the behaviour of multiple drivers may thus be created by detecting behaviour of the drivers, e.g. via a PND associated with their vehicle, and transmitting the data to a central server. The central server may then aggregate the information to obtain aggregate workload parameters for different points of an electronic map, and reference the parameters to appropriate e.g. nodes or segments of the map. This may be referred to as a generic workload map layer.

It will be appreciated that the profile may contain workload information for all nodes or sets of segments, or only certain manoeuvres or sets of segments in the map, e.g. those which are relatively complex. It is envisaged that the profile may be valid for a particular time. For example, it may be based upon data collected in respect of manoeuvres performed, or the traversal of sets of segments at a particular time of day, week or month, or under certain environmental conditions. For example, different profiles may then be obtained for use during day, night, week days, weekends, or when it is raining or fine weather, etc.

The generic driver workload profile, or parameter, provides a baseline indication of workload which, in accordance with embodiments of the invention is varied using an individual modifier representative of the workload of an individual driver.

In accordance with the invention, the method also involves generating an individual modifier which is representative of the workload of an individual driver, and is used to determine an individual driver workload parameter indicative of the workload of the individual driver when performing the manoeuvre at a node or traversing the one or more segments of the electronic map based on the corresponding generic driver workload parameter for that manoeuvre or a traversal of the one or more segments of the electronic map.

The individual modifier may be generated at any stage. It will be appreciated that this may be generated before or after a generic driver workload profile or parameter is accessed or created. The individual modifier is a value which may be used to change the baseline value of workload indicated by the generic driver workload parameter for a given manoeuvre or the traversal of a set of segments. The individual modifier is representative of the actual real-time or historic driving behaviour of an individual driver. It may be obtained by appropriate monitoring during driving by the individual. The individual modifier may be based on any variable indicative of driving behaviour, and which is relevant to assessing driver workload. For example, as described earlier, such indicators might include parameters indicative of acceleration, deceleration, curve aggression factor, speed traveled or similar. Such parameters might indicate how smoothly or otherwise the driver is driving. Relative jerkiness of driving may indicate higher stress, and hence workload levels. Typically the detected behaviour is indicative of a driving style of the driver, e.g. relatively cautious, aggressive, risk taker, etc.

While the generic workload parameter relates specifically to the performing of a given manoeuvre or the traversal of one or more segments of an electronic map, the individual modifier may be a general indicator of the driving behaviour of an individual driver, e.g. the level of aggression, smoothness, etc, and not specific to a particular manoeuvre or traversal of one or more segments. The individual modifier might be built up over a period of e.g. a month by monitoring the individual drivers behaviour, or could be determined in real time, reflecting the driver's behaviour of a given day and time.

It is envisaged that different individual modifiers might be obtained in respect of different environmental or temporal conditions in the same manner described by reference to the generic workload parameter or profile. The relevant modifier would then be retrieved in respect of the conditions applicable when data indicative of individual driver workload is required, or at a time when a route is to be followed, etc.

In some embodiments a single individual modifier is derived for a given individual, and stored in association with data indicative of the drivers identity. In these embodiments the same individual modifier will be used whenever an individual driver workload parameter is required, regardless of the manoeuvre or segments to which it relates.

In other embodiments multiple individual modifiers are generated. These can then be stored in appropriate database in conjunction with data regarding the applicability of a modifier. Different modifiers may be generated for different sets of conditions, e.g. time of day, weather condition, etc. It is also envisaged that different individual modifiers might be generated for application to different manoeuvres or sets of one or more segments. For example, a user may have stored a favourite route. It can be assumed that this is a route with which the driver is familiar, and which they will travel frequently. Accordingly, the familiarity may result in a lower workload for the driver when following that route. A different modifier may be generated specifically for determining the individual driver workload parameters in respect of any manoeuvre or segments along that route i.e. in respect of the traversal of segments thereof, or a manoeuvre at a node thereon. For example, this might be an appropriate lower percentage of the standard individual modifier.

In more complex arrangements, a given individual modifier may be used in relation to determining individual driver workload parameters in respect of manoeuvres or the traversal of sets of segments that can be grouped together, based upon common attributes. The attributes may be based upon individual driver behaviour, and the workload experienced by the individual for different types of manoeuvre or types of route. For example, if a given driver finds left turns on curved road segments to be difficult, any such traversals may be associated with a given individual modifier that will lead to relatively higher individual workload values being determined.

It will be appreciated that for simplicity, only one, where a limited number of individual modifiers is generated for an individual driver. These may then be used to modify the generic driver workload parameter in respect of a given manoeuvre or traversal of a set of one or more segments of an electronic map. As these are used to modify generic driver workload parameters which form part of a generic driver workload profile incorporating variation over different regions of an electronic map, the generic profile will ensure variation in the resulting individual driver workload parameters derived based thereon, even if the individual modifier does not vary of the different regions. In other words, the baseline provided by the generic driver workload profile will vary. This avoids the need to determine the many different individual modifiers, or to determine individual modifiers in respect of specific manoeuvres or traversals of given segments of the map.

In accordance with the invention, the individual modifier is used with the generic driver workload parameter for a given manoeuvre or traversing of a set of one or more segments to provide an individual driver workload parameter for that manoeuvre or traversal of the one or more segments. This may be carried out in a suitable manner and is typically provided by obtaining a function of the generic driver workload parameter, and the individual modifier. The individual modifier indicates the way in which the generic driver workload profile should be varied to account for the individual drivers behaviour. In some simple cases, the individual modifier may provide a value which is subtracted from or added to the generic driver workload parameter, or a factor by which it is to be multiplied to increase or decrease the parameter to account for the individual differences. In basic terms, the individual modifier will act to increase or decrease the workload associated with a given manoeuvre or traversal of a set of segments based upon the generic parameter.

The individual modifier or modifiers may or may not be stored. Likewise, an individual workload parameter or parameters determined may or may not be stored.

In one example, the or each individual modifier is stored, and used when required to obtain an individual user workload parameter based on the generic workload parameter associated with a given manoeuvre or set of segments. The individual modifier may be stored in association with data indicative of the drivers identity. The modifier may then be retrieved whenever it is detected or the system is informed that the given driver is driving.

In another example, an individual modifier may be used with a generic workload profile to obtain an individual workload profile including a respective parameter for each manoeuvre or set of segments in relation to which a generic workload parameter was present in the generic profile. The individual workload profile may be stored in association with data indicative of the individual's identity, and then retrieved when that individual is driving.

In yet another example, individual modifiers may be used to obtain individual workload parameters in respect of individual manoeuvres or sets of segments based on corresponding generic workload parameters from a generic workload profile, and the individual parameters stored for use when those manoeuvres or segments are encountered, without forming an entire individual workload profile.

The steps of the method may be carried out in various locations. For example, determination of individual modifiers may be carried out by a server. The modifiers may then be transmitted to an in-vehicle system, e.g. PND as required, for example to determine individual user workload parameters e.g. in respect of a planned route, or for use in determining a user workload profile. Alternatively or additionally, the modifier might be stored by the in-vehicle system. Where an individual driver workload profile is determined, this may be carried out by a server or in-vehicle system, and may be stored by the in-vehicle system or server. Where individual modifiers are determined in real-time based on individual driver behaviour, this may be carried out by a server or in-vehicle system. The latter arrangement may be more efficient of bandwidth if the in-vehicle system collects the driving behaviour data. Of course, steps may be carried out elsewhere, e.g. by a computer apparatus to which a driver connects their PND, etc.

Once the individual driver workload parameter has been determined, it may be used appropriately. As mentioned above, an individual driver workload profile may be obtained for different manoeuvres or segments in a geographic area represented by an electronic map.

In some embodiments, the individual driver workload parameter is provided to an in-vehicle system, such an ADAS, integrated navigation device or PND, and used to control its operation. This may be in terms of controlling communication with a driver. For example, where the individual driver workload parameter for a given upcoming or current manoeuvre is high, a navigation device may be controlled so as to change the way in which it provides navigation instructions so as to reduce the amount of information the user is presented at a given time, or to enhance the clarity of the instructions. When an individual driver workload parameter is relatively high, certain functions of an in-vehicle system e.g. audio functions, telephone capability may be disabled. Conversely, where workload is relatively low the functions may be enabled, or a PND, when giving navigation instructions may provide a greater density of instructions, or more detailed instructions.

Another option would be for a warning or alert to be provided to the driver in respect of an upcoming manoeuvre or section of a route being followed that is associated with a high workload. Further examples of the way in which workload may be used include adapting the user interface of a PND or other in-vehicle display, e.g. showing more or less information, or map details, or changing a contrast level. A particular application of the system may be disabled when driver workload is high, e.g. incoming calls might be delayed or handled differently, potentially depending upon whether or not the caller is known to the driver. In another example, accessing non-driving applications e.g. voice controlled e-mail, might be allowed when workload is low. Speed advice might be provided based on workload, or advice as to a safe distance to be maintained with respect to a vehicle ahead. Conversely, if workload is relatively low, such that a user might be at risk of losing concentration, or even falling asleep, some kind of warning may be given.

A workload level might be displayed to a user. This might be a current workload, or an expected workload in respect of certain positions on a map. Individual workload parameters may be used to provide an individual workload profile, which can be presented to a user illustrating variation in workload in respect of a calculated route, or over the area of an electronic map. This may allow a user to choose routes which are associated with lower workloads.

Various techniques are known for adapting the operation of a PND, integrated navigation device, ADAS, or other in-vehicle system in accordance with workload, and are exemplified, e.g. in WO 2008/004857 A1, or WO 2009/143903 A1. In general terms, the system may be controlled so as to reduce the amount of mental capacity of a driver that it demands where workload is, or is expected to be high, or to increase the amount of mental capacity required when workload is low.

FIG. 1 is a schematic diagram illustrating these steps in a method in accordance with the invention. In step 1, a generic driver workload profile is created, and stored in memory, e.g. locally on a device or remotely at a server (for subsequent retrieval by a device). In step 2, an individual driver modifier is generated based on data indicative of the drivers behaviour. In step 3, the individual driver modifier is used with a generic driver workload parameter for performing a given manoeuvre or traversing one or more segments of an electronic map obtained from the generic workload profile to determine an individual driver workload parameter for the manoeuvre or traversal. In step 4, the individual workload parameter is used to control operation of an in-vehicle system.

Some examples of the way in which individual driver workload parameters may be obtained and stored will now be given.

In one embodiment, the individual modifier is a single modifier, which is applicable to determine any individual driver workload parameter associated with a manoeuvre at a node or the traversal of one or more segments of an electronic map. In other words, the individual modifier does not change from location to location. For example, it may be determined that the modifier is 0.95 indicating that the driver is relatively experienced, or smooth in their driving, as determined by their driving behaviour, and thus a relatively lower workload than that indicated by the generic profile should be used for the driver. Such a modifier may be used together with the generic driver workload profile to obtain an individual driver workload profile. This may be achieved by simply multiplying each generic driver workload parameter of the profile by the modifier to obtain an appropriate individual driver workload parameter. These values may be stored as a new data layer associated with an electronic map.

For example, a generic driver workload profile might indicate that at a node, the generic driver workload parameter is 50. In this example, the individual modifier is 0.95, which would provide an individual driver workload parameter for that node of 0.95×50=47.5. This type of individual driver workload profile may then be stored in association with information identifying the driver, and may be used to load the workload information as required for that driver. In this example, it is envisaged that the modifier might not itself be stored, but only the data indicative of the individual driver workload parameters. These might be stored in the form of a modified individual driver profile.

In another arrangement, the individual modifier might be stored, and used when required to modify generic driver workload parameters, e.g. associated with a generic driver workload profile. For example, when a given node is to be traversed, the individual modifier may be accessed, and used to adjust the generic driver workload parameter for that node.

In other arrangements, more than one individual modifier might be derived, in respect of different types of manoeuvre, or the traversal of different sets of segments in an electronic map. For example, certain categories of manoeuvres or sets of segments might be determined, which, on the basis of an individual drivers behaviour, are considered to be more or less stressful to the individual. A specific modifier may then be derived for each category of nodes/manoeuvres or segments.

In these arrangements the generic driver workload parameter may be used for all manoeuvres or regions of an electronic map other than those falling into a certain category, which has been identified as being associated with a relatively lower or higher workload for the individual. These might be manoeuvres of a certain type. However, it is has been found that manoeuvres or sets of segments in respect of which a given modifier would be appropriate can be more readily determined by consideration of the driving behaviour of an individual driver over different regions of the map. In these arrangements a given modifier might be stored in association with information indicative of the type of node, manoeuvre or segments to which it relates. One modifier might be derived for a city type segment, or a set of segments with certain properties, e.g. involving a tunnel and left turn or similar, which are particularly challenging for the individual driver.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A method of determining data indicative of an individual driver workload, the method comprising:
   obtaining generic driver workload data, the generic driver workload data being representative of a generic driver workload when performing a manoeuvre at a node or traversing a set of one or more segments of an electronic map;
   generating an individual modifier representative of the behaviour of an individual driver, the individual modifier being proportional to likely deviation of an individual workload of the driver from corresponding generic workloads of drivers when performing manoeuvres or traversing segments; and
   using the individual modifier to determine individual driver workload data indicative of the workload of the individual driver when performing the manoeuvre at the node or traversing the one or more segments of the electronic map based on the generic driver workload data for the manoeuvre at the node or the traversal of the one or more segments.

2. The method of claim 1, wherein the generic driver workload data is a generic driver workload parameter, and the individual driver workload data is an individual driver workload parameter.

3. The method of claim 1, wherein the generic driver workload data is based upon data indicative of the behaviour of multiple drivers when performing the manoeuvre and/or traversing the one or more segments.

4. The method of claim 1, wherein the generic driver workload data forms part of a generic driver workload profile comprising data indicative of a generic workload of drivers when performing each of plurality of different manoeuvres at a node or nodes and/or traversing a plurality of sets of one or more segments of the electronic map, wherein the generic driver workload data for a given manoeuvre and/or traversal of a set of one or more segments is associated with electronic map data indicative of the manoeuvre or the set of one or more segments.

5. The method of claim 1, wherein the step of determining the individual modifier comprises generating the individual modifier using data representative of the real-time or historic behaviour of the individual driver, or combinations thereof.

6. The method of claim 5, further comprising obtaining the data representative of the behaviour of the individual driver, wherein the data collected automatically during driving by the individual driver.

7. The method of claim 1, wherein the individual modifier is generated using data indicative of any one of the acceleration, deceleration, curve aggression factor, speed or braking of the driver.

8. The method of claim 1, wherein the manoeuvre at the node or traversal of a set of one or more segments of the electronic map is a first manoeuvre at a node or traversal of a set of one or more segments of the electronic map, and
the method further comprises obtaining data indicative of an individual driver workload for at least one further manoeuvre at a node and/or the traversal of at least one further set of one or more segments of the electronic map,
wherein the method comprises determining the individual driver workload data based on generic driver workload data for the at least one further manoeuvre at a node and/or the traversal of at least one further set of one or more segments of the electronic map using the individual modifier generated in relation to determining the individual driver workload data in respect of the first manoeuvre at a node or traversal of a set of one or more segments of the electronic map.

9. The method of claim 8,
wherein the first manoeuvre at the node or traversal of a set of one or more segments of the electronic map and the at least one further manoeuvre at a node and/or the traversal of at least one further set of one or more segments of the electronic map share one or more common attributes by reference to the behaviour of the individual driver or
wherein the first manoeuvre at a node or traversal of a set of one or more segments of the electronic map and the at least one further manoeuvre at a node and/or the traversal of at least one further set of one or more segments of the electronic map are associated with a given predetermined route.

10. The method of claim 1,
wherein the manoeuvre at the node or the traversal of the set of one or more segments of the electronic map forms part of a first predetermined route, and
the method further comprises obtaining data indicative of an individual driver workload for at least one further manoeuvre at a node and/or the traversal of at least one further set of one or more segments of the electronic map which do not form part of the first predetermined route,
wherein the method comprises generating a further individual modifier for use in determining the individual driver workload data based on generic driver workload data for the at least one further manoeuvre at a node and/or the traversal of at least one further set of one or more segments of the electronic map using the individual modifier, and
using the further individual modifier to determine the individual driver workload data based on the generic driver workload data.

11. The method of claim 1, wherein the individual driver workload parameter is a function of the individual modifier and the generic driver workload data for the manoeuvre at the node or the traversal of the one or more segments.

12. The method of claim 1, comprising storing individual driver workload data in association with electronic map data indicative of the manoeuvre or set of one or more segments to which it relates and/or storing the individual modifier.

13. The method of claim 1, comprising using individual driver workload data obtained in respect of different manoeuvres at a node or nodes and/or the traversal of different sets of segments of the electronic map to provide an individual driver workload profile indicative of the workload of the individual driver when performing each of a plurality of different manoeuvres at a node or nodes and/or traversing a plurality of sets of one or more segments of the electronic map.

14. The method of claim 1 wherein the individual modifier is specific to a set of one or more environmental and/or temporal conditions.

15. The method of claim 1 further comprising using the individual workload data to control the operation of an in-vehicle system, optionally an ADAS or navigation system.

16. A non-transitory computer readable medium comprising computer readable instructions, which, when executed on a computer, cause the computer to perform a method for determining data indicative of an individual driver workload, the method comprising:
obtaining generic driver workload data, the generic drive workload data being representative of a generic driver workload when performing a manoeuvre at a node or transversing a set of one or more segments of an electronic map,
generating an individual modifier representative of the behaviour of an individual driver, the individual modifier being proportional to a likely deviation of an individual workload of the driver from corresponding generic workloads of drivers when performing manoeuvres or traversing segments; and
using the individual modifier to determine individual driver workload data indicative of the workload of the individual driver when performing the manoeuvre at the node or traversing the one or more segments of the electronic map based on the generic driver workload data for the manoeuvre at the node or the traversal of the one or more segments.

17. A system for determining data indicative of an individual driver workload, the system comprising:
one or more processors; and
a memory comprising instructions which, when executed by the one or more processors, cause the system to:
obtain generic driver workload data, the generic driver workload data being representative of a generic driver workload when performing a manoeuvre at a node or traversing a set of one or more segments of an electronic map;
generate an individual modifier representative of the behaviour of an individual driver, the individual modifier being proportional to a likely deviation of an individual workload of the driver from corresponding generic workloads of drivers when performing manoeuvres or traversing segments; and use the individual modifier to determine individual driver workload data indicative of the workload of the individual driver when performing the manoeuvre at the node or traversing the one or more segments of the electronic map based on the generic driver workload data for the manoeuvre at the node or the traversal of the one or more segments.

18. The computer readable medium of claim 16 further comprising using the individual workload data to control the operation of an in-vehicle system.

19. The system of claim 17, wherein the system further provides the individual workload data to an in-vehicle system.

* * * * *